US009056291B2

(12) United States Patent
Battrell et al.

(10) Patent No.: US 9,056,291 B2
(45) Date of Patent: Jun. 16, 2015

(54) MICROFLUIDIC REACTOR SYSTEM

(75) Inventors: C. Frederick Battrell, Redmond, WA (US); John Clemmens, Redmond, WA (US); Isaac Sprague, Bellevue, WA (US)

(73) Assignee: Micronics, Inc., Redmond, WA (US)

( * ) Notice: Subject to any disclaimer, the term of this patent is extended or adjusted under 35 U.S.C. 154(b) by 693 days.

(21) Appl. No.: 13/346,615

(22) Filed: Jan. 9, 2012

(65) Prior Publication Data
US 2012/0177543 A1    Jul. 12, 2012

Related U.S. Application Data

(60) Continuation-in-part of application No. 12/341,637, filed on Dec. 22, 2008, now Pat. No. 8,110,392, which is a continuation of application No. PCT/US2007/014522, filed on Jun. 22, 2007, (Continued)

(51) Int. Cl.
*B01L 3/00* (2006.01)
*B01F 11/00* (2006.01)
(Continued)

(52) U.S. Cl.
CPC ......... *B01F 11/0071* (2013.01); *B01F 11/0074* (2013.01); *B01F 13/0059* (2013.01); *B01L 3/502715* (2013.01); *B01L 3/50273* (2013.01); *B01L 3/502738* (2013.01); *B01L 2200/027* (2013.01); *B01L 2200/0689* (2013.01); *B01L 2300/0636* (2013.01); *B01L 2300/069* (2013.01); *B01L 2300/0816* (2013.01); *B01L 2300/0867* (2013.01); *B01L 2300/0887* (2013.01);
(Continued)

(58) Field of Classification Search
CPC ............ B01F 11/0071; B01F 13/0059; B01L 2300/0816; B01L 2400/0481; B01L 3/50273; B01L 3/502738; B01L 3/502761; G01N 2035/00564
See application file for complete search history.

(56) References Cited

U.S. PATENT DOCUMENTS 3,933,997 A    1/1976   Hersh et al.
3,970,518 A    7/1976   Giaever
(Continued)

FOREIGN PATENT DOCUMENTS

DE    202004012163 U1    11/2004
WO    88/08534 A1        11/1988
(Continued)

OTHER PUBLICATIONS

Carter et al., "Short Exposure Time Sensitivity of White Cells to Shear Stress," *ASAIO Journal* 49:687-691, 2003.
(Continued)

*Primary Examiner* — Melanie Y Brown
*Assistant Examiner* — Erik B Crawford
(74) *Attorney, Agent, or Firm* — Seed IP Law Group PLLC

(57) ABSTRACT

A compact device for operatively coupling a solid planar substrate, for example a glass slide, to a microfluidic circuit and performing a reaction or reactions on organic matter bound to the face of the planar substrate. Typical reactions include binding, staining and/or labeling reactions. In use, a sealed reaction chamber is formed, the chamber enclosing the organic matter and at least a part of the solid substrate. Headspace in the sealed chamber between the solid substrate is generally of microfluidic dimensions, and diaphragm pump members are used to inject, exchange and/or mix the fluids in the chamber.

18 Claims, 19 Drawing Sheets

Related U.S. Application Data application No. 13/346,615, which is a continuation-in-part of application No. 13/099,187, filed on May 2, 2011, which is a continuation of application No. 12/685,546, filed on Jan. 11, 2010, now Pat. No. 7,955,836, which is a division of application No. 11/562,611, filed on Nov. 22, 2006, now Pat. No. 7,763,453.

(60) Provisional application No. 60/816,204, filed on Jun. 23, 2006, provisional application No. 60/740,697, filed on Nov. 30, 2005.

(51) Int. Cl.
*B01F 13/00* (2006.01)
*F04B 43/02* (2006.01)
*F04B 43/04* (2006.01)
*F04B 43/06* (2006.01)
*G01N 33/543* (2006.01)

(52) U.S. Cl.
CPC .. *B01L2400/0481* (2013.01); *B01L 2400/0638* (2013.01); *F04B 43/02* (2013.01); *F04B 43/043* (2013.01); *F04B 43/06* (2013.01); *G01N 33/54366* (2013.01)

(56) References Cited

U.S. PATENT DOCUMENTS

| | | |
|---|---|---|
| 3,996,345 A | 12/1976 | Ullman et al. |
| 4,018,886 A | 4/1977 | Giaever |
| 4,104,029 A | 8/1978 | Maier, Jr. |
| 4,230,685 A | 10/1980 | Senyei et al. |
| 4,235,960 A | 11/1980 | Sasse et al. |
| 4,267,234 A | 5/1981 | Rembaum |
| 4,366,241 A | 12/1982 | Tom et al. |
| 4,373,932 A | 2/1983 | Gribnau et al. |
| 4,452,773 A | 6/1984 | Molday |
| 4,554,088 A | 11/1985 | Whitehead et al. |
| 4,654,267 A | 3/1987 | Ugelstad et al. |
| 4,659,678 A | 4/1987 | Forrest et al. |
| 4,810,630 A | 3/1989 | Craig et al. |
| 4,837,168 A | 6/1989 | de Jaeger et al. |
| 5,100,626 A | 3/1992 | Levin |
| 5,141,850 A | 8/1992 | Cole et al. |
| 5,160,701 A | 11/1992 | Brown, III et al. |
| 5,252,459 A | 10/1993 | Tarcha et al. |
| 5,415,994 A | 5/1995 | Imrich et al. |
| 5,639,428 A | 6/1997 | Cottingham |
| 5,658,723 A | 8/1997 | Oberhardt |
| 5,670,381 A | 9/1997 | Jou et al. |
| 5,681,339 A | 10/1997 | McEwen et al. |
| 5,716,852 A | 2/1998 | Yager et al. |
| 5,718,567 A | 2/1998 | Rapp et al. |
| 5,922,591 A | 7/1999 | Anderson et al. |
| 5,972,710 A | 10/1999 | Weigl et al. |
| 6,037,168 A | 3/2000 | Brown |
| 6,158,712 A | 12/2000 | Craig |
| 6,168,948 B1 | 1/2001 | Anderson et al. |
| 6,272,939 B1 | 8/2001 | Frye et al. |
| 6,287,850 B1 | 9/2001 | Besemer et al. |
| 6,303,389 B1 | 10/2001 | Levin et al. |
| 6,309,875 B1 | 10/2001 | Gordon |
| 6,326,211 B1 | 12/2001 | Anderson et al. |
| 6,431,212 B1 | 8/2002 | Hayenga et al. |
| 6,432,212 B1 | 8/2002 | Hirose et al. |
| 6,468,807 B1 | 10/2002 | Svensson et al. |
| 6,488,896 B2 | 12/2002 | Weigl et al. |
| 6,541,213 B1 | 4/2003 | Weigl et al. |
| 6,569,674 B1 | 5/2003 | McGarry et al. |
| 6,581,899 B2 | 6/2003 | Williams |
| 6,729,352 B2 | 5/2004 | O'Connor et al. |
| 6,743,399 B1 | 6/2004 | Weigl et al. |
| 6,843,263 B2 | 1/2005 | Kuo et al. |
| 6,872,566 B2 | 3/2005 | Vischer et al. |
| 6,899,137 B2 | 5/2005 | Unger et al. |
| 6,916,113 B2 | 7/2005 | Van de Goor et al. |
| 7,052,594 B2 | 5/2006 | Pelrine et al. |
| 7,223,363 B2 | 5/2007 | McNeely et al. |
| 7,223,371 B2 | 5/2007 | Hayenga et al. |
| 7,235,400 B2 | 6/2007 | Adey |
| 7,318,912 B2 | 1/2008 | Pezzuto et al. |
| 7,763,453 B2 | 7/2010 | Clemmens et al. |
| 7,906,317 B2 | 3/2011 | Lee et al. |
| 2002/0029814 A1 | 3/2002 | Unger et al. |
| 2002/0148992 A1 | 10/2002 | Hayenga et al. |
| 2002/0160518 A1 | 10/2002 | Hayenga et al. |
| 2002/0187560 A1 | 12/2002 | Pezzuto et al. |
| 2003/0119057 A1 | 6/2003 | Gascoyne et al. |
| 2003/0124619 A1 | 7/2003 | Weigl et al. |
| 2003/0129756 A1 | 7/2003 | Thorne et al. |
| 2003/0175980 A1 | 9/2003 | Hayenga et al. |
| 2003/0175990 A1 | 9/2003 | Hayenga et al. |
| 2004/0037739 A1 | 2/2004 | McNeely et al. |
| 2005/0013732 A1 | 1/2005 | Battrell et al. |
| 2005/0019898 A1 | 1/2005 | Adey et al. |
| 2005/0106066 A1 | 5/2005 | Saltsman et al. |
| 2006/0003440 A1 | 1/2006 | Streit et al. |
| 2006/0127886 A1 | 6/2006 | Kaylor et al. |
| 2006/0166375 A1 | 7/2006 | Hawkins et al. |
| 2006/0246575 A1 | 11/2006 | Lancaster et al. |
| 2007/0042427 A1 | 2/2007 | Gerdes et al. |
| 2007/0183935 A1 | 8/2007 | Clemmens et al. |
| 2010/0112723 A1 | 5/2010 | Battrell et al. |

FOREIGN PATENT DOCUMENTS

| | | |
|---|---|---|
| WO | 91/12336 A1 | 8/1991 |
| WO | 96/33399 A1 | 10/1996 |
| WO | 01/70381 A2 | 9/2001 |
| WO | 02/01184 A1 | 1/2002 |
| WO | 02/40874 A1 | 5/2002 |
| WO | 02/41994 A2 | 5/2002 |
| WO | 03/015923 A1 | 2/2003 |
| WO | 2005/016529 A1 | 2/2005 |
| WO | 2005/106024 A1 | 11/2005 |
| WO | 2007/064635 A1 | 6/2007 |
| WO | 2008/002462 A2 | 2/2008 |

OTHER PUBLICATIONS

Cuzzubbo A. J., et al., "Use of Recombinant Envelope Proteins for Serological Diagnosis of Dengue Virus Infection in an Immunochromatographic Assay," *Clin. Diagn. Lab. Immunol.* 8(6):1150-1155, 2001.

Dewitz et al., "Mechanical trauma in leukocytes," *J. Lab. Clin. Med.* 90(4):728-736, Oct. 1977.

Fuentes et al., "Detecting minimal traces of DNA using DNA covalently attached to superparamagnetic nanoparticles and direct PCR-ELISA," *Biosensors and Bioelectronics* 21:1574-1580, 2006.

Hardt, S., et al., "Passive micromixers for applications in the microreactor and µTAS fields," *Microfluid Nanofluid* 1:108-118, 2005.

Hashimoto, S., "Erythrocyte Destruction under Periodically Fluctuating Shear Rate: Comparative Study with Constant Shear Rate," *Artificial Organs* 13(5):458-463, 1989.

Jacobs J. A., et al., "Detection of *Streptococcus pneumoniae* Antigen in Bronchoalveolar Lavage Fluid Samples by a Rapid Immunochromatographic Membrane Assay," *J. Clin. Microbiol.* 43(8):4037-4040, 2005.

Kameneva et al., "Effects of Turbulent Stresses upon Mechanical Hemolysis: Experimental and Computational Analysis," *ASAIO Journal* 50:418-423, 2004.

Kennedy, J. H., et al., "Protein-Protein Coupling Reactions and the Applications of Protein Conjugates," *Clinica Chimica Acta* 70:1-31, 1976.

Khan, A., et al., "Antibiotic Resistance, Virulence Gene, and Molecular Profiles of Shiga Toxin-Producing *Escherichia coli* Isolates from Diverse Sources in Calcutta, India," *J. Clin. Microbiol.* 40(6):2009-2015, Jun. 2002.

(56) References Cited

OTHER PUBLICATIONS

Khan, A., et al., "Prevalence and Genetic Profiling of Virulence Determinants of Non-O157 Shiga Toxin-Producing *Escherichia coli* Isolated from Cattle, Beef, and Humans, Calcutta, India," *Emerging Infectious Diseases* 8(1):54-62, Jan. 2002.

Kittigul, L., et al., "Use of a Rapid Immunochromatographic Test for Early Diagnosis of Dengue Virus Infection," *Eur. J. Clin. Microbiol. Infect. Dis.* 21:224-226, 2002.

Lu et al., "Microfluidic Shear Devices for Quantitative Analysis of Cell Adhesion," *Analytical Chemistry* 76(18):5257-5264, Sep. 15, 2004.

Matas et al., "Transition to turbulence in particulate pipe flow," *Phys. Rev. Lett.* 90(1):14501-14504, 2003.

Nielsen, S. L., et al., "Detection of Immunoglobulin G Antibodies to Cytomegalovirus Antigens by Antibody Capture Enzyme-Linked Immunosorbent Assay," *J. Clin. Microbiol.* 24(6):998-1003, Dec. 1986.

Ohta, K., et al., "Enzyme-Linked Immunosorbent Assay of Influenza Specific IgA Antibody in Nasal Mucus," *Acta Paediatr Jpn.* 33(5):617-622, Oct. 1991.

Platt et al., "Exercise-Induced Hemolysis in Sickle Cell Anemia: Shear Sensitivity and Erythrocyte Dehydration," *Blood* 59(5):1055-1060, May 1982.

Porstmann B., et al., "Comparison of Chromogens for the Determination of Horseradish Peroxidase as a Marker in Enzyme Immunoassay," *J. Clin. Chem. Clin. Biochem.* 19(7):435-439, 1981.

Schmid-Schoenbein et al., "Microscopy and viscometry of blood flowing under uniform shear rate (rheoscopy)," *Journal of Applied Physiology* 26(5):674-678, May 1969.

Shaikh et al., "A modular microfluidic architecture for integrated biochemical analysis," *PNAS* 102(28):9745-9750, Jul. 12, 2005.

Sirigireddy et al., "Multiplex Detection of *Ehrlichia* and *Anaplasma* Species Pathogens in Peripheral Blood by Real-Time Reverse Transcriptase-Polymerase Chain Reaction," *Journal of Molecular Diagnostics* 7(2):308-316, May 2005.

Staben et al., "Particle transport in Poiseuille flow in narrow channels," *International Journal of Multiphase Flow* 31:529-547, 2005.

Tai, D.-F., et al., "Artificial Receptors in Serologic Tests for the Early Diagnosis of Dengue Virus Infection," *Clinical Chemistry* 52(8):1486-1491, 2006.

Unger M. A., et al., "Monolithic Microfabricated Valves and Pumps by Multilayer Soft Lithography," *Science* 288:113-116, Apr. 7, 2000.

Wolf et al., "Rapid hybridization kinetics of DNA attached to submicron latex particles," *Nucleic Acids Research* 15(7):2911-2926, 1987.

Yogi S., et al. "Clinical Evaluation of the Bladder Tumor Marker "TU-MARK-BTA"" *Acta Urol. Jpn.* 37(4):335-339, 1991 (English Abstract).

English abstract for DE 202004012163, Questel Database, Oct. 7, 2004.

International Preliminary Report on Patentability for PCT/US2006/045529, dated Jun. 3, 2008, 7 pages.

International Search Report and Written Opinion for PCT/US2006/045529, mailing date Mar. 29, 2007, 14 pages.

International Search Report for PCT/US2007/014522, mailed Mar. 4, 2008, 7 pages.

*Fig. 4*
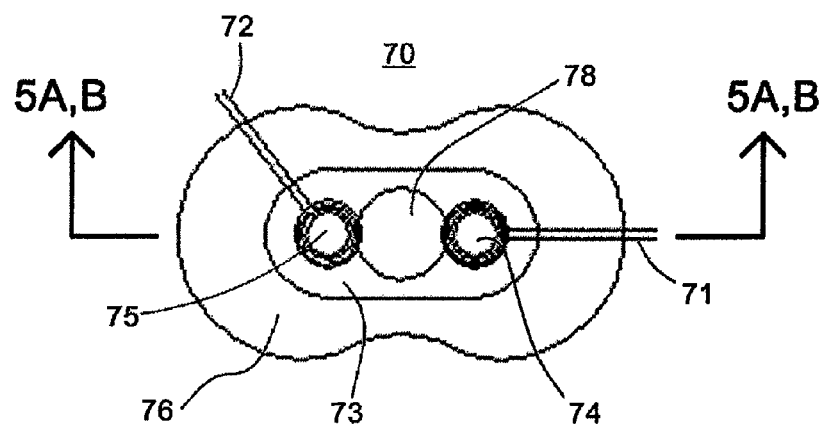
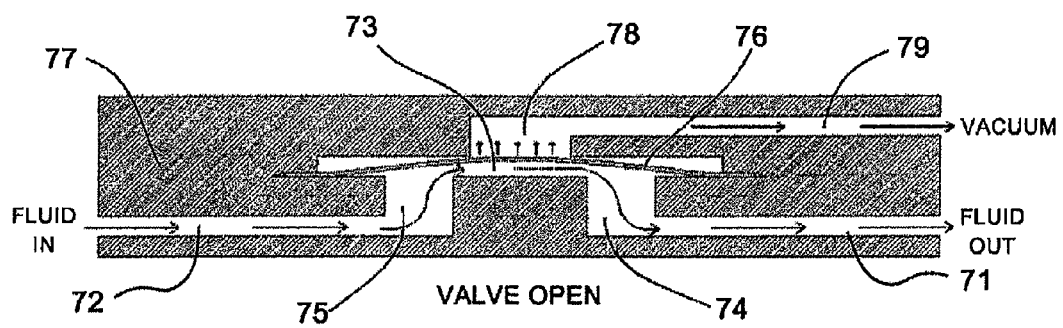
*Fig. 5A*
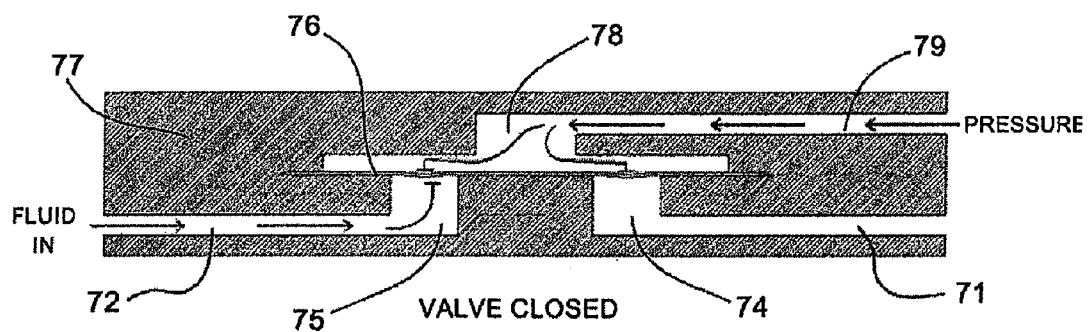
*Fig. 5B*

Relaxed State

Waste Filling the Chamber

| PUMP CHAMBER DIAMETER D1 | PUMP CHAMBER RESTING VOLUME | PUMP CHAMBER STROKE DISPLACEMENT |
|---|---|---|
| ~5700 um | ~55 uL | ± ~45 uL |

| APERTURE WIDTH Y1 (um) | APERTURE DEPTH Z1 (um) | APERTURE LENGTH L1 (um) |
|---|---|---|
| ~1000 um | ~1800 um | ~1500 um |

A. Negative Control
B. Positive for Agglutination
C. Negative Control

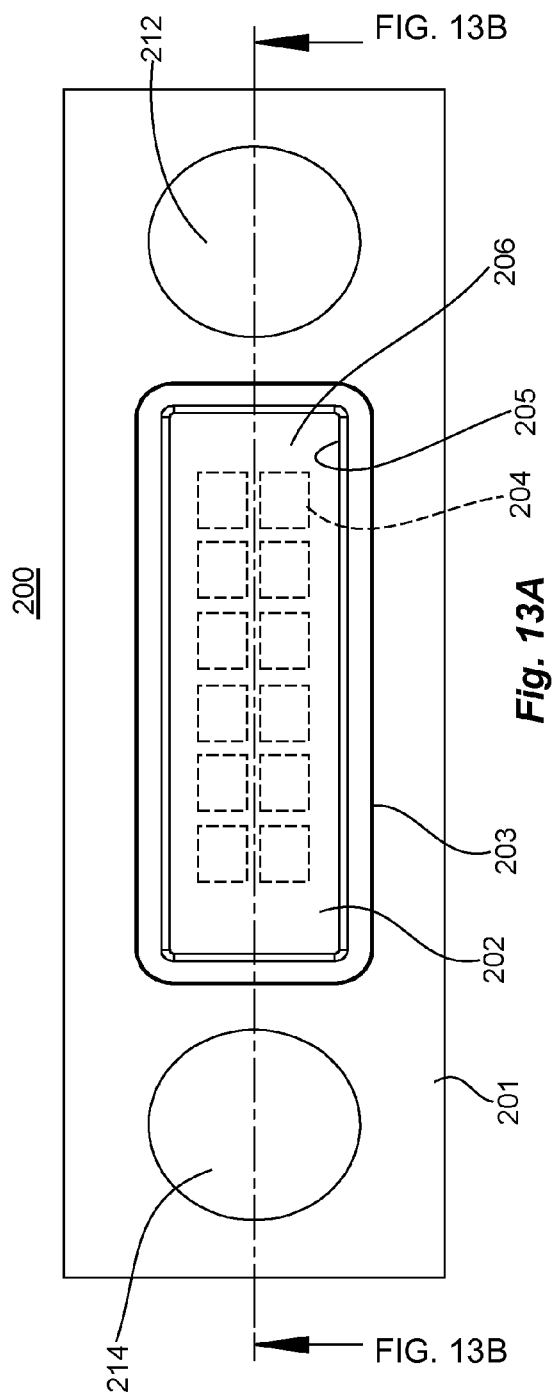
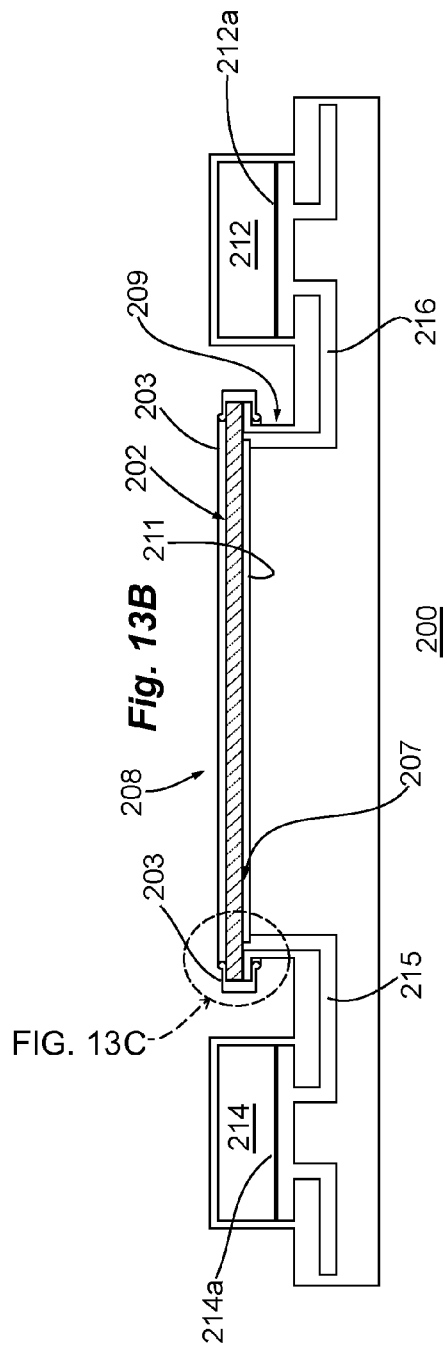
Fig. 13A
Fig. 13B

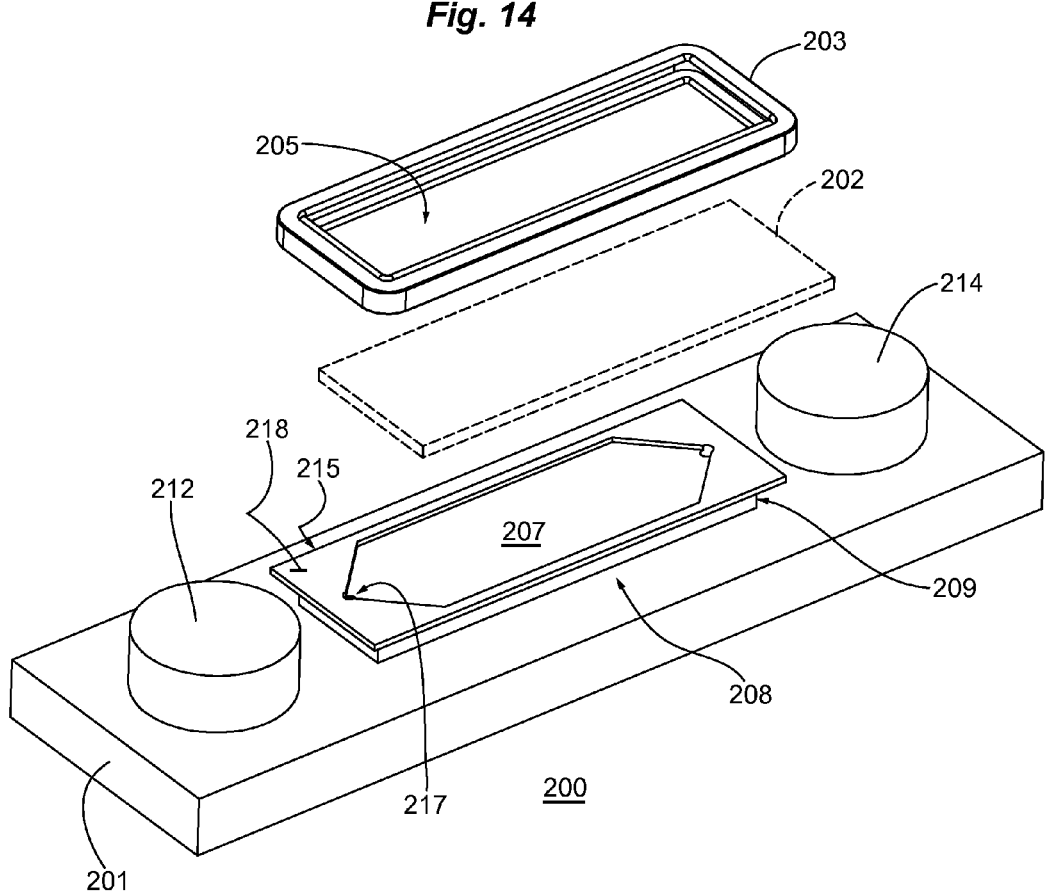
*Fig. 14*
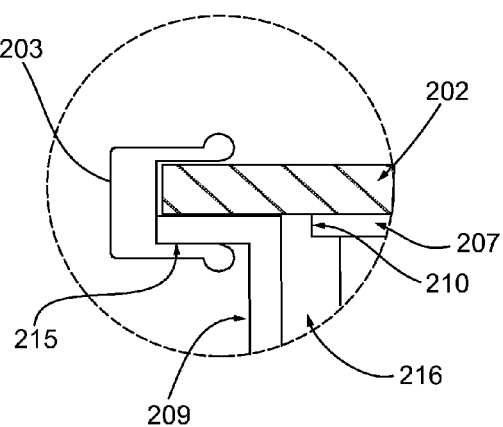
*Fig, 13C*

MICROFLUIDIC REACTOR SYSTEM

CROSS-REFERENCE TO RELATED APPLICATIONS

This application is a Continuation-In-Part of U.S. patent application Ser. No. 12/341,637, filed Dec. 22, 2008, now allowed, which is a continuation of International Application No. PCT/US2007/014522, filed on Jun. 22, 2007, which claims the benefit under 35 U.S.C. 119(e) of U.S. Provisional Patent Application No. 60/816,204, filed Jun. 23, 2006. This application is a Continuation-In-Part of U.S. patent application Ser. No. 13/099,187, filed on May 2, 2011, now pending, which is a continuation of U.S. patent application Ser. No. 12/685,546, filed on Jan. 11, 2010, now issued as U.S. Pat. No. 7,955,836, which is a divisional of U.S. patent application Ser. No. 11/562,611, filed Nov. 22, 2006, now issued as U.S. Pat. No. 7,763,453, which claims the benefit under 35 U.S.C. 119(e) of U.S. Provisional Patent Application No. 60/740,697, filed on Nov. 30, 2005. All said patent documents are each incorporated herein by reference in their entireties as if set forth in full herein.

BACKGROUND

1. Technical Field

The present invention relates the general field of biological assays, and more particularly to a microfluidic apparatus for conducting cellular, enzymatic, chemical and molecular biological processes on a solid substrate, generally a glass slide.

2. Description of the Related Art

Detection of biomarkers at the point of care (such as, for example, in the field, in remote areas, in a doctor's office, and at the bedside in a hospital) has the potential to offer real time diagnostic information, improve patient care outcomes, decrease sample volumes, and provide analytical information from a broad range of biological samples, many of which may be acquired relatively non-invasively.

Co-assigned patents and patent applications relevant to the development of clinical assays in a microfluidic device test format include PCT Publication No. WO200201184 ("Fluid Mixing in Microfluidic Structures"), U.S. Pat. No. 6,743,399 ("Pumpless Microfluidics"), U.S. Pat. No. 6,488,896 ("Microfluidic Analysis Cartridge"), U.S. Patent Application Publication No. 20050106066 ("Microfluidic Devices for Fluid Manipulation and Analysis"), U.S. Patent Application Publication No. 20020160518 ("Microfluidic Sedimentation"), U.S. Patent Application Publication No. 20030124619 ("Microscale Diffusion Immunoassay"), U.S. Patent Application Publication No. 20030175990 ("Microfluidic Channel Network Device"), U.S. Patent Application Publication No. 20050013732 ("Method and System for Microfluidic Manipulation, Amplification and Analysis of Fluids, For Example, Bacteria Assays and Antiglobulin Testing"), U.S. Pat. No. 6,581,899 ("Valve for Use in Microfluidic Structures"), and PCT Publication No. WO2007/064635 ("Microfluidic Cell Capture and Mixing Circuit"), all of which are hereby incorporated by reference in their entireties. Also incorporated herein by reference is U.S. Pat. No. 6,729,352, which relates to microfluidic valve structures.

Capillary action has proven useful in designing small disposable diagnostic devices, as discussed in, for example, U.S. Pat. No. 5,415,994, U.S. Pat. No. 5,658,723 and PCT Publication No. WO199633399. However, to improve sensitivity, mixing during affinity capture is likely to be helpful. Mixing small volumes, however, is not without unique problems. The problem of mixing in a microvolume is variously addressed in, for example, U.S. Pat. Nos. 6,468,807, 6,916,113, 6,872,566 and 6,729,352 (which describes a "slit mixer") and also in Hardt, S. et al. ("Passive Micromixers for Applications in the Microreactor and µTAS Fields", Microfluid Nanofluid, vol. 1:108-118, 2005).

Further related art includes the Maui® Mixer sold by BioMicro Systems and described in PCT Publication No. WO2003015923, U.S. Patent Application Publication No. 20050019898 and U.S. Pat. No. 7,223,363. The teaching of these disclosures relates particularly to use of a pair of flexible bladders mounted at each end of a rectilinear microfluidic chamber and a gasketed assembly for sealing the chamber to a glass slide. Preferred dimensions are given, and the claims are generally directed to a rectilinear chamber with parallel sides. In particular, the height of the chamber is generally 10 to 500 µm and the height is small relative to the length and to the width. The walls of the chamber are selected to be smooth and to run parallel to the axis of flow so as to avoid trapping of air bubbles and reduced mixing efficiency. U.S. Pat. Nos. 5,100,626 and 6,303,389 also teach parallel channel walls.

Mixing is achieved with sonication in U.S. Pat. No. 6,326,211 and with agitation in U.S. Pat. No. 6,309,875. See also PCT Publication Nos. WO200201184 and WO200170381, and U.S. Pat. Nos. 6,287,850, 6,272,939, 6,158,712, 5,922,591 and 5,639,428. However, these methods depend on relatively large sample volumes, large hybridization chambers and inconvenient or complicated equipment not readily adapted to the point of care. Also of related interest, U.S. Pat. No. 5,718,567 describes a microscale diaphragm pump with check valves and a titanium diaphragm, U.S. Pat. No. 7,052,594 to Pelrine describes an electrically active diaphragm for use in microfluidic pumps, and U.S. Pat. No. 6,843,263 to Koh describes microfluidic cards with "a deformable chamber" having an elastic thin film cover and a mechanical actuator, the film serving to seal the body and the mechanical actuator serving to deform the film and move plugs of fluid in the body, relying on the elasticity of the film and open venting to generate reciprocal flow of the fluid plug. The pressurization of an open vented system containing hazardous sample is a serious disadvantage of the teachings of U.S. Pat. No. 5,718,567.

However, in contemplating use of disposable microfluidic device-based assays of clinical specimens, design of fully closed, "single-entry" systems has not been adequately addressed. In view of contamination hazards associated with working with potentially infectious human samples, resealable entry into the device with gasketed sealing means is often simply not acceptable. Moreover, the assay format must be robust and readily adapted for use with a wide range of biomarkers, both in automated and manual assays, at the point of care. To achieve these objectives, further improvement in mixing arts for microvolumes is needed.

Also needed are devices compatible with solid planar substrates such as glass slides, which are frequently used to mount, stain and examine tissue specimens, cell specimens, and to screen DNA and protein arrays, while not limited thereto, where there is a need to promote mixing in a thin fluid layer over the specimens which may have a microfluidic dimension.

Accordingly, although there have been advances in the field, there remains a need in the art for microfluidic devices that meet the foregoing criteria. The present invention addresses these needs and provides further related advantages.

BRIEF SUMMARY

Advances in materials and miniaturization now permit the adaptation of these assays to a new generation of devices for bioassays based on microfluidics; these can be formatted either as hand-held cartridges (also termed "cards"), or as cartridges for automated or semi-automated, machine-aided testing. Microfluidic device-based assays enable small-volume sampling, with point-of-care results from a broad variety of biological fluids and samples in real time, and optionally, assay cartridges that work with single use reagent packs, or are fully self-contained and operable entirely by hand.

Complete enzyme-linked immunosorbent assay (ELISA) systems in a microfluidic device format are provided for detection of a wide spectrum of biomarker molecules. Such devices are generally disposable and low-cost. Bioassays adapted to a robust microfluidics device format include solid phase affinity-capture assays such as those based on antibody/antigen, antigen/antibody, antibody/protein A, glycomer/lectin, and, generally, signal molecule/receptor as target:affinity-capture pairs. Preferred solid phase affinity-capture assay systems for ELISA include antibody/antigen, antigen/antibody, antibody/protein A, streptavidin/avidin, and histidine/NTA target:affinity-capture pairs. Enzyme-linked antibodies, antigens, streptavidin, and histidine-rich proteins are generally available or may be synthesized by techniques well known in the art. Detection systems for immunoaffinity capture and tagging or amplification of target biomarker signals include, for example, enzyme-linked conjugates and chromogenic substrates (immunochromogenic and ELISA-type detection), streptavidin-enzyme conjugates (again with ELISA-type or immunochromogenic detection), antibody-coupled beads, antigen-coupled beads (with immunoprecipitin or agglutination-type detection), protein A-coupled beads, streptavidin-coupled beads, and enzyme- or bead-conjugated protein-histidine-nickel chelates. Beads for tagging can be colored, fluorescent, luminescent, tagged with radiofrequency transmitters, or otherwise labeled so that binding or agglutination can be readily detected. Titrations and binding neutralization assays also provide detectable endpoints. The microfluidic device-based immunoassays disclosed here also anticipate the use of magnetic beads in affinity concentration steps or mixing.

Mixing of small volumes as required to contact the target analyte with the solid-phase affinity capture agent and with reagents is accomplished with diaphragm pumps, herein termed "bellows pumps", useful to generate reciprocating flow across the affinity capture site, which is placed between a pair of such pumps. Stagnant liquid is broken up by use of "flow constricting" or "flow focusing" apertures positioned between the pumps and the central chamber containing the affinity capture site or sites, eliminating the need for impellers and reducing incubation time. Mean flow velocity is increased by the focusing apertures, causing exit plume microeddies characteristic of turbulent or near-turbulent flow that aid mixing, an inventive adaptation of a Penberthy eductor to a micro-scale. This mixing method is referred to herein as "micro-eductive mixing" or "eductive mixing". By pairing bellows pumps inside the body of a microfluidic device, the system can be completely closed (without venting) during operation, a useful precaution against operator exposure to the contents of the device.

As a device or apparatus, disclosed herein is a combination of a first bellows pump fluidly connected by a first flow constricting aperture to an assay chamber and an opposing second bellows pump fluidly connected by a second flow constricting aperture to the assay chamber, wherein the bellows pumps are configured with pneumatic actuators for tandem operation whereby fluid is pumped back and forth through the assay chamber without venting, and further wherein the first and second flow constricting apertures are configured for micro-eductive mixing, the assay chamber further comprising an affinity capture site for heterogeneous binding assay.

As an operational process, disclosed herein is a method for heterogeneous binding assay in a microfluidic device, comprising the steps of: pumping a fluidized sample containing a target analyte back and forth across an affinity capture site without venting, said pumping step further comprising micro-eductive mixing with tandem bellows pumps; and detecting bound target analyte.

For example, in one embodiment, a microfluidic card for performing heterogeneous binding assays is disclosed, comprising: a) a first bellows pump fluidly connected by a first flow constricting aperture to an assay chamber; and b) a second bellows pump fluidly connected by a second flow constricting aperture to said assay chamber, wherein: i) said first and second bellows pumps comprise pneumatic actuators for tandem operation whereby fluid is pumped back and forth through said assay chamber without venting; ii) said first and second flow constricting apertures are configured for micro-eductive mixing; and iii) said assay chamber further comprises an affinity capture site for heterogeneous binding assay.

In a further embodiment, said card further comprises: a) a plastic card body with external surfaces encasing: i) said first bellows pump, wherein said first bellows pump comprises a first pump cavity bisected in coronal plane by a first flexible diaphragm, said first flexible diaphragm dividing said first pump cavity into an upper half-chamber and a lower half-chamber; ii) said second bellows pump, wherein said second bellows pump comprises a second pump cavity bisected in coronal plane by a second flexible diaphragm, said second flexible diaphragm dividing said second pump cavity into an upper half-chamber and a lower half-chamber; and iii) said assay chamber, wherein said assay chamber has a volume V2 and further comprises a test field with immobilized affinity agent and a transparent cover, wherein both of said lower half-chambers of said first and second bellows pumps are adapted for receiving a fluid, and wherein both of said lower half-chambers of said first and second bellows pumps have a volume V1 and a diameter D1; and b) a first actuator channel pneumatically connected to said upper half-chamber of said first bellows pump and a second actuator channel pneumatically connected to said upper half-chamber of said second bellows pump, wherein said first and second actuator channels are adapted for connection to an off-card pneumatic pressure source such that the first and second flexible diaphragms are pneumatically actuated in alternation, thereby generating reciprocating flow of a fluid between the lower half-chambers of said first and second bellows pumps and through said first and second flow constricting apertures and said assay chamber, wherein: x) said first flow constricting aperture has a maximum width Y1, a maximum depth Z1, and a length L1, and fluidly connects said lower half-chamber of said first bellows pump to said assay chamber; y) said second flow constricting aperture also has a maximum width Y1, maximum depth Z1, and length L1, and fluidly connects said lower half-chamber of said second bellows pump to said assay chamber; and z) ratios Z1/D1 and Y1/D1 are less than 0.5.

In yet a further embodiment, each of said first and second flexible diaphragms are comprised of an elastomeric film sealingly affixed to said plastic card body so as to isolate fluid within said plastic card body from said external surfaces.

In yet a further embodiment, the microfluidic card further comprises sanitary means selected from the group consisting of: a) sanitary means for fluid porting; b) sanitary means for air venting; c) sanitary means for valving; and d) sanitary means for capturing waste.

In yet a further embodiment, said sanitary means for fluid porting comprises a sample inlet port adapted for single entry of a sample fluid without contamination of said external surfaces.

In yet a further embodiment, said sanitary means for air venting comprises a gas-permeable:water impermeable filter barrier configured to prevent escape of fluid from the microfluidic card.

In yet a further embodiment, said sanitary means for valving comprises: a) a microcavity in said plastic card body, said microcavity having an upper wall, a lower rim and a bottom plate; b) a first microfluidic channel entering said microcavity through said bottom plate at a first via; c) a second microfluidic channel entering said microcavity through said bottom plate at a second via, said first and second vias separated by a valve sill; d) a flexible film attached to said lower rim around the full circumference of said microcavity, said film having a first surface facing said bottom plate, and a second surface facing said upper wall, said flexible film configured to alternate between a first position, wherein said first surface of said film is sealingly seated against both said first and second vias and said valve sill, and a second position, wherein said second surface of said film is contacting said upper wall; and e) a microfluidic pneumatic control channel entering said microcavity through said upper wall and configured to supply positive and negative pressure to said microcavity, thereby actuating said sanitary means for valving by moving said flexible film between said first position and said second position while isolating fluid within said plastic card body from said external surfaces.

In yet a further embodiment, said sanitary means for capturing waste comprises: a) a waste receiving reservoir having a waste fluid channel end and a vent end; b) an absorbent bat disposed within said waste receiving reservoir and contacting said waste fluid channel end; and c) a flexible film disposed within said waste receiving reservoir and having a first side facing said absorbent bat and a second side facing said vent end, wherein said flexible film is sealed to said plastic body such that said flexible film separates said vent end and said waste fluid channel end, wherein said vent end comprises a vent exiting said external surface of said plastic body.

In yet a further embodiment, said vent further comprises a gas-permeable:water impermeable filter barrier.

In yet a further embodiment, said volume V1, diameter D1, and said aperture dimensions Y1, Z1, and L1 are configured for micro-eductive mixing.

In a second embodiment, a microfluidic card comprising an on-board waste fluid isolation apparatus is disclosed, said on-board waste fluid isolation apparatus comprising: a) a plastic body having an external surface and encasing a waste receiving reservoir having a waste fluid channel end and a vent end; b) an absorbent bat disposed within said waste receiving reservoir and contacting said waste fluid channel end; and c) a flexible film separatingly disposed within said waste receiving reservoir and having a first side facing said absorbent bat and a second side facing said vent end, wherein said flexible film is sealed to said plastic body such that said flexible film isolatingly separates said waste fluid channel end and said vent end, wherein said vent end further comprises a vent exiting said external surface of said plastic body.

In a further embodiment, said vent further comprises a gas-permeable:water impermeable filter barrier.

In a third embodiment, a kit for performing a heterogeneous binding assay on a clinical sample is disclosed comprising a microfluidic card of the foregoing embodiments.

In a fourth embodiment, a kit for performing a heterogeneous binding assay on a clinical sample is disclosed comprising a microfluidic card of the foregoing embodiments.

In a fifth embodiment, a method for performing heterogeneous binding assays in a microfluidic device is disclosed comprising the steps of: a) pumping a fluidized sample comprising a target analyte back and forth across an affinity capture site between tandem bellows pumps without venting; and b) detecting target analyte bound on said affinity capture site, wherein said pumping step further comprises pumping said fluidized sample through an aperture and micro-eductively mixing said fluidized sample.

In a further embodiment, said step for detecting a target analyte bound on said affinity capture site comprises detecting a bound chromogenic or fluorescent tag.

In another further embodiment, said step for detecting a target analyte bound on said affinity capture site comprises detection by direct or indirect ELISA.

In a sixth embodiment, a microfluidic card for performing agglutination assays is disclosed comprising a serpentine channel, an affinity capture agent comprising a bead or cell, and an optical window for detecting an agglutination reaction upstream from an on-board waste fluid isolation apparatus.

In a further embodiment, said on-board waste fluid isolation apparatus comprises: a) a plastic body having an external surface and encasing a waste receiving reservoir having a waste fluid channel end and a vent end; b) an absorbent bat disposed within said waste receiving reservoir and contacting said waste fluid channel end; and c) a flexible film separatingly disposed within said waste receiving reservoir and having a first side facing said absorbent bat and a second side facing said vent end, wherein said flexible film is sealed to said plastic body such that said flexible film isolatingly separates said waste fluid channel end and said vent end, wherein said vent end further comprises a vent exiting said external surface of said plastic body. In yet a further embodiment, said vent further comprises a gas-permeable:water impermeable filter barrier.

Alternate embodiments are also presented. In a first alternate embodiment, disclosed is an apparatus for sealingly enclosing a first aspect of a substrate member in a reaction chamber and reacting organic matter bound thereon, the apparatus comprising: a) a baseplate member having a first surface, wherein the first surface comprises a platform medially disposed thereon, the platform having a top surface dimensioned for contactingly receiving the first aspect of the substrate member in juxtaposition with the top surface thereof, and outside edges and outside lateral wall surfaces therearound, wherein the top surface is interrupted by a recess defined by interior walls having a height ranging from 5 to 100 micrometers, a recessed slab connecting the bottom edges of the interior walls, and a flat boundary ledge connecting the top edges of the interior walls and the outside edges of the platform, the flat ledge for supporting the first aspect of the substrate member thereon, whereby a reaction chamber with headspace volume is formed between the recessed slab and the first aspect of the substrate member when sealed to the flat ledge; b) a gasket member fitted to the outside edges of the platform, and c) a pair of bellows pumps comprising a first bellows pump and a second bellows pump, the first bellows pump having a first fluidic connection to the reaction chamber and the second bellows pump having a second fluidic connection to the reaction chamber, at least one of said first and second bellows pumps having one or more fluidic connections to one or more reagent reservoirs or vents disposed outside the reaction chamber, wherein the pairs are disposed to drive fluid flow into, across and through said reaction chamber, thereby injecting, exchanging and mixing the fluids in the chamber.

The first aspect of a substrate member is generally a planar face of a plate-like solid, such as a glass slide or a silicon chip. In one view, the planar face of the substrate can form a lid over the reaction chamber; in another view the reaction chamber can form a lid over the planar face, and the reaction chamber is thus a shallow tray enclosing a volume between two juxtaposed surfaces. The reaction chamber encloses organic matter bound to the face of the planar substrate exposed to the sealed chamber so that it is wetted by liquid reagents passed through its volume, which is variable in length and width, but is of a generally microfluidic dimension in depth.

Generally, a first bellows pump will be fluidically connected to a first volume of said headspace volume and said second bellows pump will be fluidically connected to a second volume of said headspace volume. The bellows pumps thus form a pair; multiple pairs of bellows pumps may be used. The bellows pumps may be pneumatically driven. Pneumatic actuation may include a positive stroke and a negative suction stroke. In one embodiment, a reciprocating flow across the face of the substrate member is driven by repetitively actuating the first and second bellows pumps by applying a positive pressure pulses to each said bellows pumps in alternation. In a preferred embodiment, reciprocating flow may also be driven by applying a positive pressure pulse to the first bellows pump and a suction pressure pulse to the second bellows pump, and then reversing the polarity of the pressure pulses applied to each bellows pump. Alternatively, the bellows pumps may be magnetically driven, as when powered by electromagnets.

In one option, the apparatus comprises a plurality of pairs of bellows pumps, each bellows pump of said pair having a fluidic connection to the reaction chamber, wherein the pairs of bellows pumps are disposed to drive fluid flow back and forth across and through the reaction chamber.

The reaction chamber may be provided with an observation window is formed in the gasket or in the baseplate, or both, thus allowing for epifluorescent and/or transmission microscopy, for example. The bellows pumps may be disposed proximate to the platform, such as laterally thereto or on top of or under the platform relative to the baseplate. The platform is generally raised above the baseplate to facilitate sealing of the reaction chamber with a gasket.

In one embodiment, the gasket member comprises a web member for coveringly and sealingly enclosing a first aspect or segment of the substrate member or glass slide on top of the boundary ledge and a peripheral skirt member for sealingly engaging the outside edges and outside lateral wall surfaces of the platform. The gasket is preferably molded of an elastomer such as a silicone or a vinyl rubber and the observation window is generally formed in the web.

In selected applications, a cutout is formed on a lateral aspect of the gasket for sealedly enclosing the first aspect of the substrate member in the reaction chamber and a projecting segment of the substrate member outside the reaction chamber, thereby exposing projecting segment outside the sealed reaction chamber. The cutout is adapted for receiving a glass slide having an electrode array junction and wire harness mounted on the exposed second segment of the glass slide.

In another alternate embodiment an apparatus is disclosed for enclosing a face or aspect of a substrate member in a sealed reaction chamber and reacting organic matter bound thereon, which comprises: a) a slide minicassette having a housing body with internal tray, gasketed peripheral rails, and end-mounted clamping members for sealingly receiving a mated substrate member and thereby forming a sealed reaction chamber, further wherein the tray is provided with a first fluidic connection adaptor and a second fluidic connection adaptor, the adaptors for establishing a fluidic channel between said sealed reaction chamber and a fluidic circuit in a baseplate module having a docking bay into which said slide minicassette reversibly inserts; b) the baseplate module having a first surface, wherein the docking bay is medially disposed thereon, the docking bay having a recessed surface dimensioned for receiving the slide minicassette, wherein the docking bay is provided with a first fluidic connection channel with sealing member and a second fluidic connection channel with sealing member, the first and second channels for forming a fluidic path through the reaction chamber when sealedly engaged with the first and second adaptors of the slide minicassette; c) a first bellows pump and a second bellows pump, the first bellows pump having a first fluidic connection to the reaction chamber and the second bellows pump having a second fluidic connection to the reaction chamber, at least one of said first and second bellows pumps having one or more fluidic connections to one or more reagent reservoirs or vents disposed outside the reaction chamber. Advantageously, the slide minicassette may be configured to be exchangeably dockable to a plurality of identical baseplate modules. Similarly, reagent reservoir or plurality of reservoirs are interchangeable, having an adaptor for removably engaging the baseplate and fluidic circuitry therein. The reagent reservoirs conveniently may be packaged in kits, each reagent reservoir having a sealed fluid therein. The adaptor for detachably attaching a reagent reservoir is a threaded nipple that sealingly engages a female receptacle in the baseplate, the female receptacle with fluidic connection to the fluidic circuitry in the baseplate. Fluid is withdrawn from the fluid reservoirs by the pumping action of the bellows pumps.

The first aspect of a substrate member is generally a planar face of a plate-like solid, such as a glass slide or a silicon chip. In one view, the planar face of the substrate can form a lid over the housing body; in another view the housing body can form a lid over the planar face of the substrate, and the reaction chamber is thus a shallow tray enclosing a volume between two juxtaposed surfaces. The minicassette encloses organic matter bound to the face of the planar substrate exposed to the sealed chamber so that it is wetted by liquid reagents passed through its volume, which is variable in length and width, but is of a generally microfluidic dimension in depth.

Generally, a first bellows pump will be fluidically connected to a first volume of said headspace volume and said second bellows pump will be fluidically connected to a second volume of said headspace volume. The bellows pumps thus form a pair; multiple pairs of bellows pumps may be used. The bellows pumps may be pneumatically driven. Pneumatic actuation may include a positive stroke and a negative suction stroke. In one embodiment, a reciprocating flow across the face of the substrate member is driven by repetitively actuating the first and second bellows pumps by applying a positive pressure pulses to each said bellows pumps in alternation. In a preferred embodiment, reciprocating flow may also be driven by applying a positive pressure pulse to the first bellows pump and a suction pressure pulse to the second bellows pump, and then reversing the polarity of the pressure pulses applied to each bellows pump. Alternatively, the bellows pumps may be magnetically driven, as when powered by electromagnets. The reaction chamber may be provided with an observation window is formed in the gasket or in the baseplate, or both, thus allowing for epifluorescent and/or transmission microscopy, for example.

In one option, the apparatus comprises a plurality of pairs of bellows pumps, each bellows pump of said pair having a fluidic connection to the reaction chamber, wherein the pairs of bellows pumps are disposed to drive fluid flow back and forth across and through the reaction chamber.

The baseplate module and the slide minicassette are configured to be operated in a vertical orientation, a horizontal orientation, or an inverted orientation, and may be interfaced with an automated apparatus for performing multiple substrate member-based reactions in parallel.

These and other aspects of the invention will be evident upon reference to the following detailed description and attached drawings.

BRIEF DESCRIPTION OF THE FIGURES

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 4 is a plan view of a microfluidic, pneumatic shutoff valve.

FIGS. 5A and 5B are section views of a microfluidic, pneumatic shutoff valve with open and closed positions shown.

FIGS. 13A-B are a plan and cross-sectional view of a first apparatus for staining a glass slide, the apparatus having dual bellows pumps acting in tandem to produce reciprocating flow through a sealed reaction chamber formed on the face of the glass slide. FIG. 13C is a detail showing placement of the edge seal member.

Not shown for clarity are valves and conventional features of fluidic circuits as would be known to one skilled in the art or may incorporated by reference from the documents cited herein.

FIG. 14 is an exploded view of the apparatus of FIG. 13.

Figure 15:
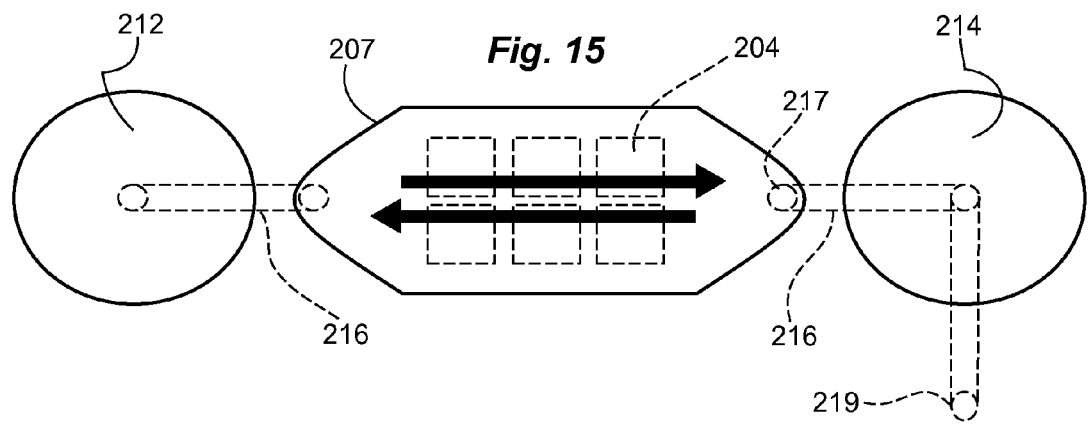

FIG. 15 is a schematic view showing dual bellows pumps and fluid flows in the enclosed chamber.

Figure 16:
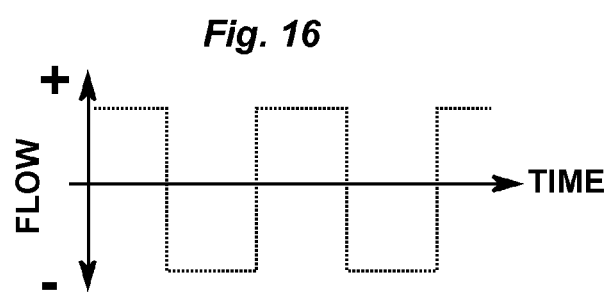

FIG. 16 is a plot showing alternating polarity of the strokes of the bellows pump diaphragms.

Figure 17A:
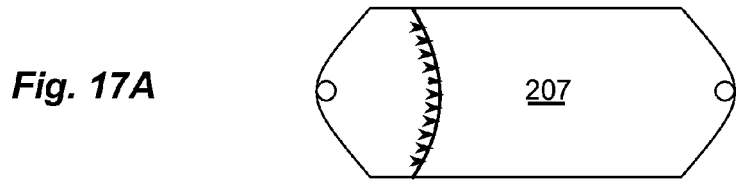
Figure 17B:
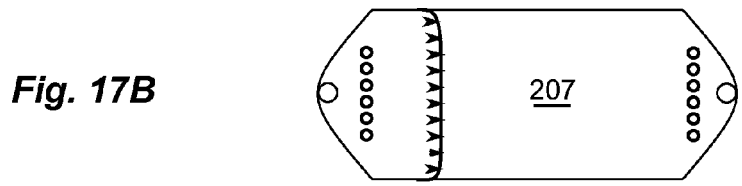
Figure 17C:
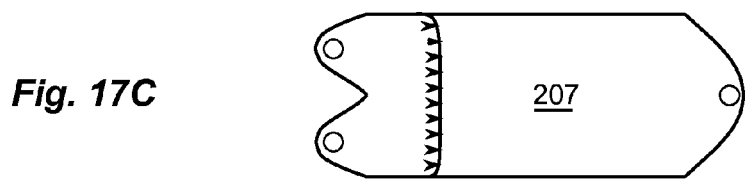

FIGS. 17A-C diagrammatically different configurations and the effect on fluid advancing through the sealed reaction chamber.

Figure 18A:
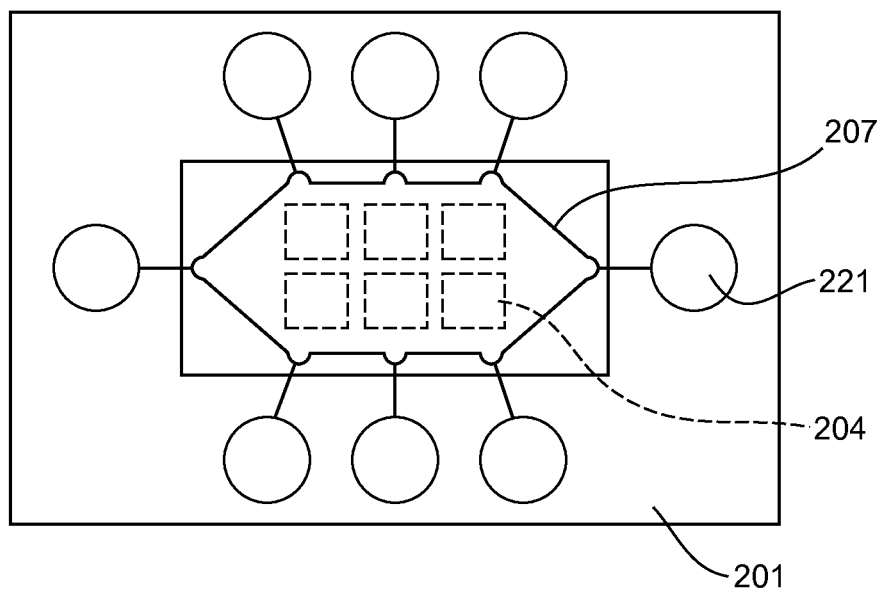
Figure 18B:
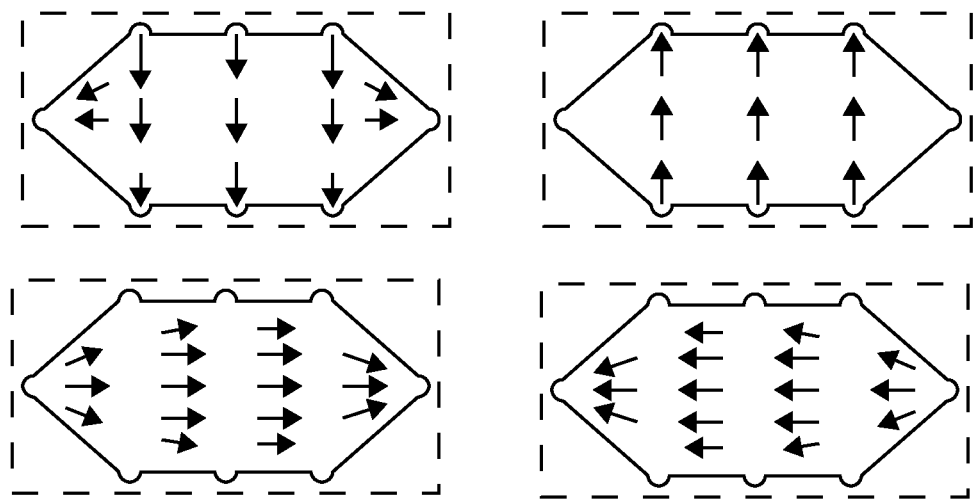

FIGS. 18A-B diagrammatically represent different configurations of paired bellows pumps and flow patterns in the sealed reaction chamber.

Figure 19:
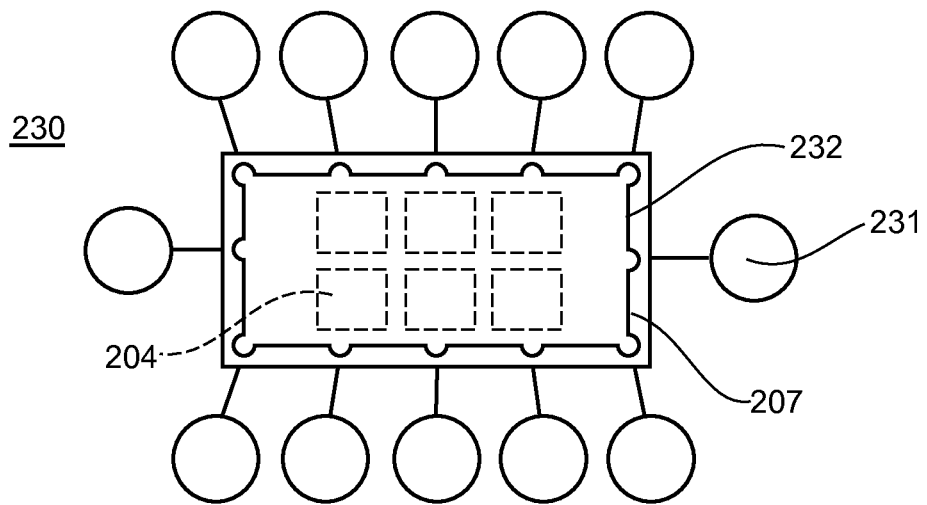

FIG. 19 depicts yet another configuration of paired bellows pumps for achieving coordinated complex mixing patterns.

Figure 20A:
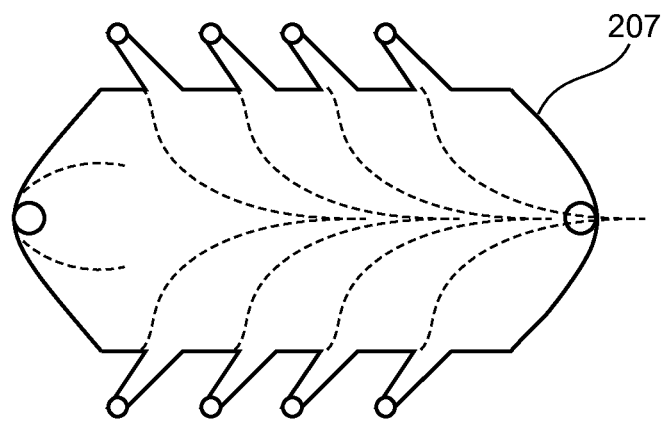

FIG. 20A is a schematic of multiple flows in a sealed reaction chamber.

Figure 20B:
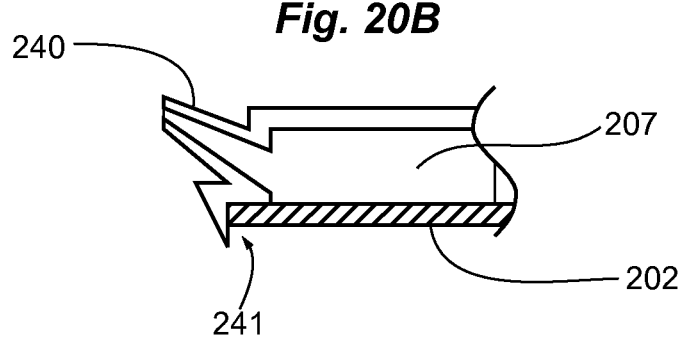

FIG. 20B is an alternate form of an injector port as may be supplied with tubulation for attachment to a bellows pump.

FIGS. 21A-21F depict means for clamping, means for sealing, and means for releasing a cover plate of a sealed reaction chamber from a substantially planar substrate to which it is affixed.

Figure 22A:
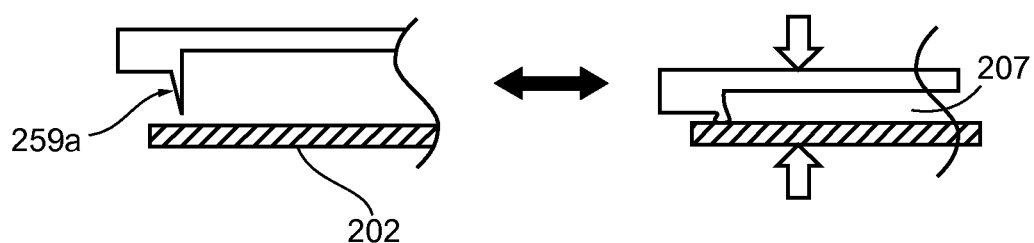
Figure 22B:
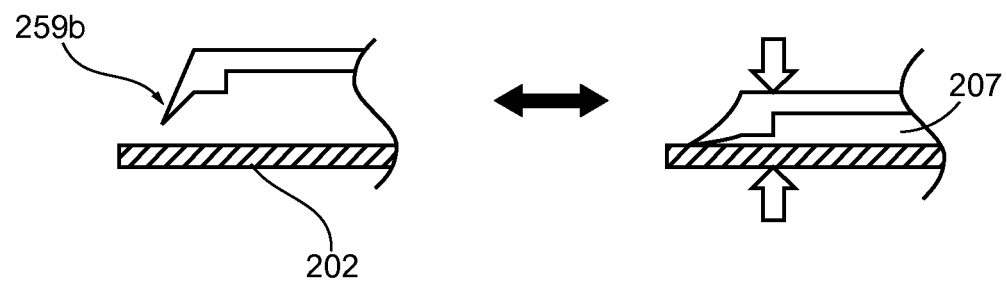

FIGS. 22A and 22B depict micromolded lip seal means for sealingly forming a sealed reaction chamber.

Figure 23A:
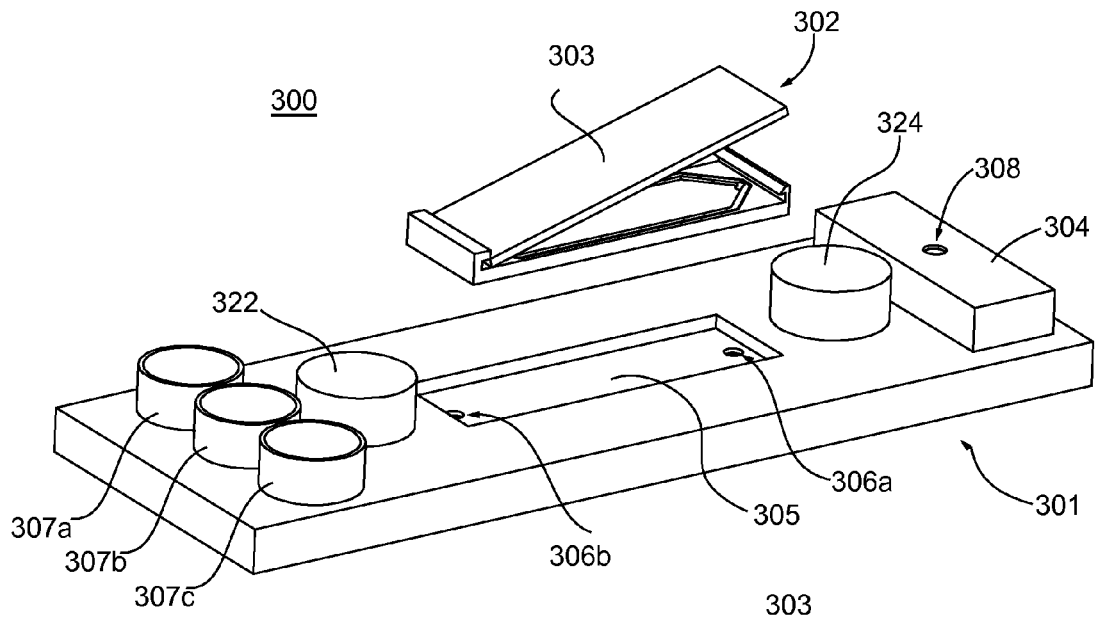
Figure 23B:
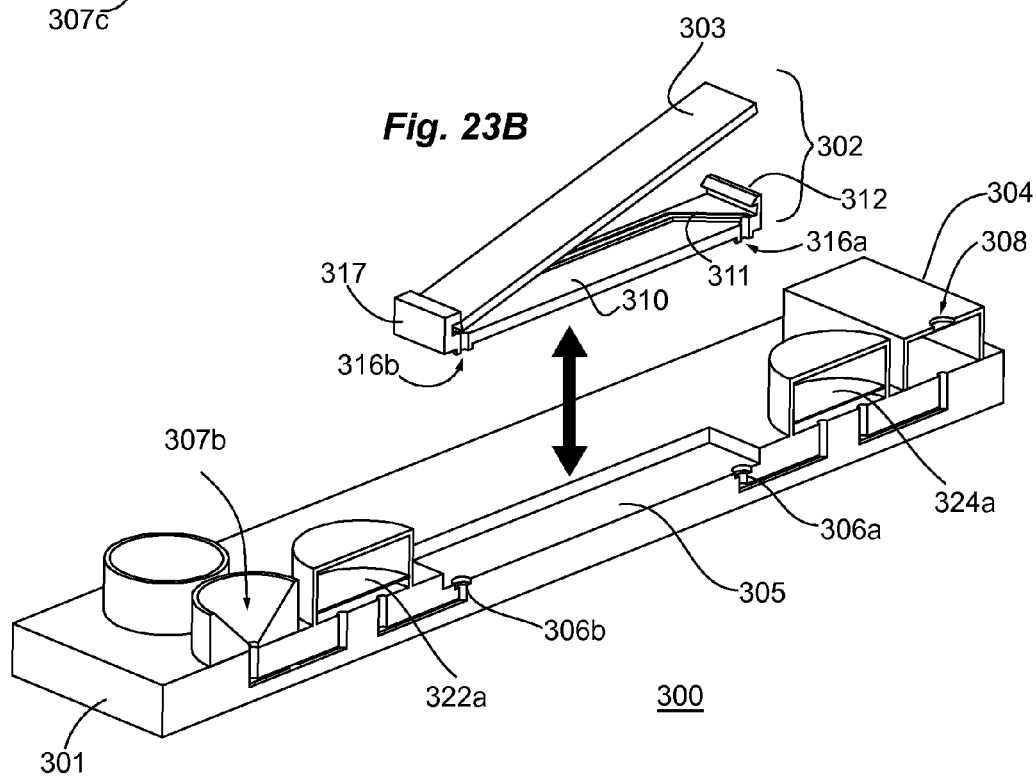

FIGS. 23A and 23B show a representative embodiment of the invention having a detachably insertable slide chamber minicassette and multiple reagent reservoirs with waste storage capacity on board.

Figure 24:
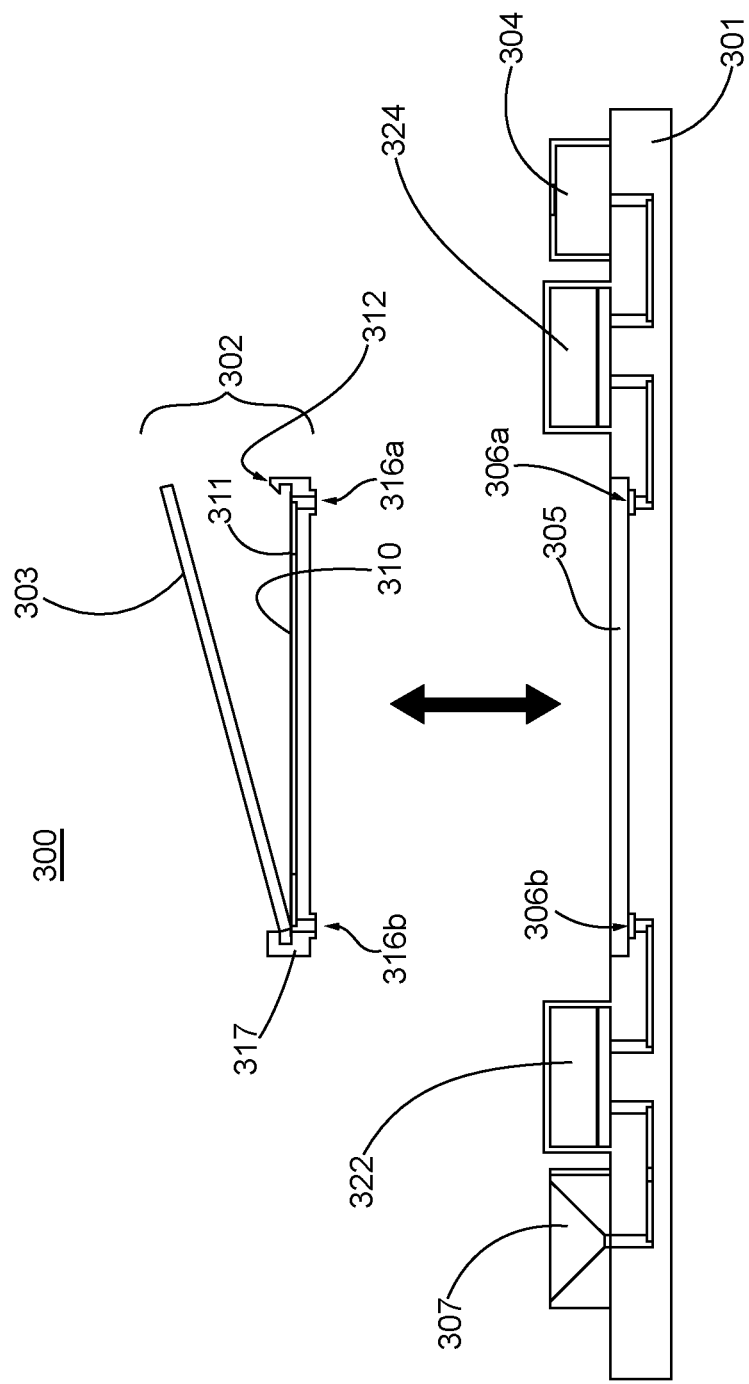

FIG. 24 is a cross-sectional view of the embodiment of FIG. 23.

Figure 25:
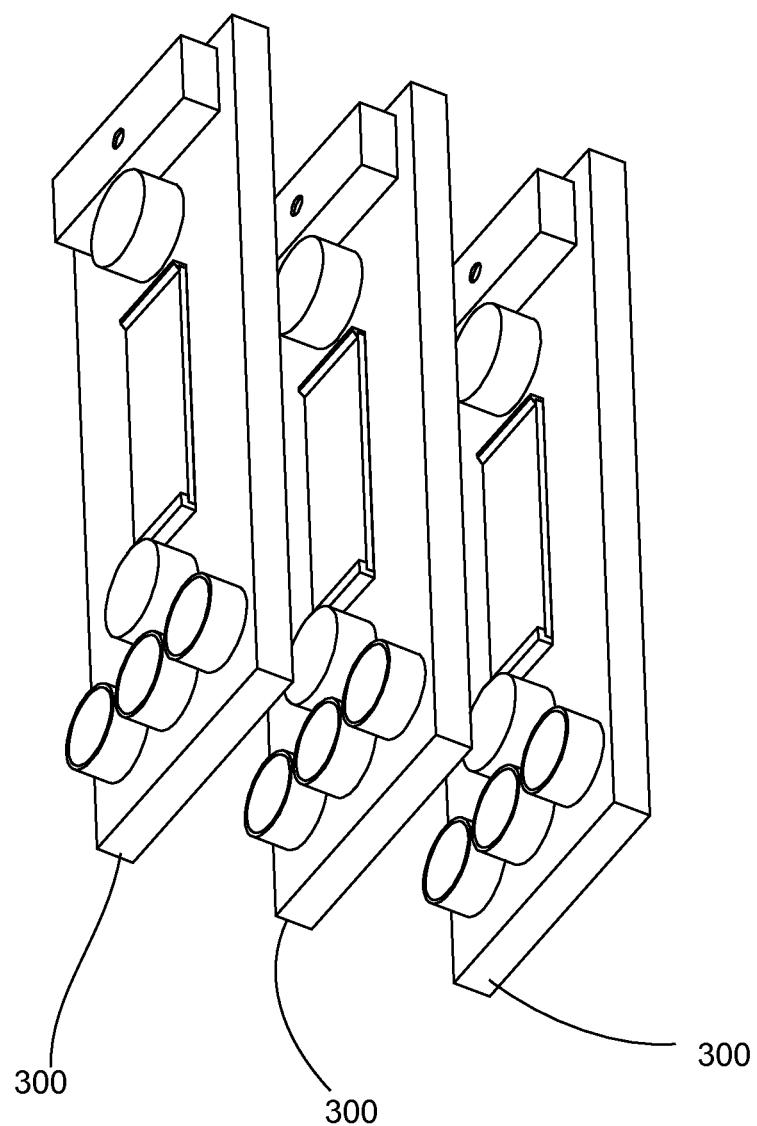

FIG. 25 illustrates a plurality of apparatus modules for use in a carousel or other automated system. Advantageously the modules are mounted in a vertical position to aid in purging bubbles.

DETAILED DESCRIPTION OF THE INVENTION

The following definitions are provided as an aid in interpreting the claims and specification herein. All of U.S. patents, U.S. patent application publications, U.S. patent applications, foreign patents, foreign patent applications and nonpatent publications referred to in this specification and/or listed in the Application Data Sheet are incorporated herein by reference, in their entirety. Where such works, incorporated herein by reference, and definitions contained therein are inconsistent in part or in whole with those supplied here, the definition used therein may supplement but shall not supersede the definition provided herein.

"Micro-eductive mixing" refers to a unique method of mixing at a microscale, whereby the ejectate of a diaphragm-actuated pumping chamber is channeled into an adjoining channel or chamber through a "focusing" or "flow constricting" aperture, thus forming a microscale plume which entrains or "educts" the surrounding bulk fluid. While not bound by theory, mean flow velocity and hence shear rate is increased by the focusing apertures, causing exit plume microeddies characteristic of turbulent or near-turbulent flow in the receiving chamber. This mixing method is referred to herein as "micro-eductive or eductive mixing". Stagnant liquid is broken up, eliminating the need for impellers and static mixers. By pairing bellows pumps, it is shown herein that a dual pump/dual aperture eductive mixing apparatus can be completely closed (without venting) during operation, a useful precaution against operator exposure to the contents of the device, and is bidirectional, improving efficiency.

In other words, "eductive mixing" or "micro-eductive mixing", is a process step whereby a liquid is forced through a microscale aperture and exits as a plume into a stagnant or slow moving bulk fluid, and the bulk fluid is entrained or educted into the rapidly moving plume, the plume further shedding eddies which mix with the educted fluid. The process step bears a relationship to the "Penberthy in-tank mixer" in function, but is adapted here structurally to a microscale or microfluidic device scale and format.

"Biomarker" means a molecule or molecules associated with a physiological condition of health or pathology in a vertebrate. Biomarkers may include not only the proteome, genome and metabolome of the vertebrate host, but also the proteome, genome and metabolome of normal flora or pathogenic infectious agents of the vertebrate body, including bacterial, protozoan, and viral pathogens. Preferred biomarkers include antigens and antibodies.

"Test samples" means representative biosamples including, but not limited to, blood, serum, plasma, buffy coat, wound exudates, pus, lung and other respiratory aspirates, nasal aspirates, bronchial lavage fluids, saliva, sputum, medial and inner ear aspirates, cyst aspirates, cerebral spinal fluid, feces, urine, tears, mammary secretions, ovarian contents, ascites fluid, mucous, stomach fluid, gastrointestinal contents, urethral discharge, synovial fluid, peritoneal fluid, vaginal fluid or discharge, amniotic fluid, semen or the like. Assay from swabs or lavages representative of mucosal secretions and epithelia are also anticipated, for example mucosal swabs of the throat, tonsils, gingival, nasal passages, vagina, urethra, anus, and eyes, as are homogenates, lysates and digests of tissue specimens of all sorts. Besides physiological fluids, samples of water, food products, air filtrates, and so forth may also be test specimens.

"Solid-phase capture" refers to affinity binding and concentration of an analyte or analyte:detection system complex on a solid phase particle, bead, surface, or porous adsorbent material. Solid phase capture may be achieved with immobilized antigen, antibody, avidin, nickel-NTA, lectin, or other ligand/receptor systems.

"Target analyte or antibody": Analyte is used broadly to indicate the biomarker detected by the assay, but it should be understood that antibodies may be both reagents of an assay and also analytes. By definition, the target analyte is not a reagent. For example, antibodies found in blood, mucous secretions, and tissue test samples may be diagnostic for a clinical condition. Antibodies used as detection tags are reagents. Serodiagnosis of a pathogen can occur by detection of an antibody to the pathogen. Similarly, assays may be designed to directly detect the target pathogen.

"Capture molecule or antibody" refer to reagents. Affinity capture of target analytes by capture molecules is a useful concentrating and detection means in microfluidic device-based assays. Targets include analytes, ligands or antibodies. Capture molecules and their respective target analyte pairs include antibody/antigen, antigen/antibody, antibody/protein A, glycomer/lectin, signal molecule/receptor, and histidine:nickel chelates. These are termed "target:affinity-capture pairs".

"Immunosorbent" is understood in the context of an analyte-sorbent complex or antibody-sorbent complex for use in immunoassays as a solid-phase capture surface. Preferred sorbent materials have relatively high surface areas and are wettable under assay conditions. Sorbent materials that have been successfully "decorated" with capture agent or antibody include agarose in bead form, such as Sephadex, other carbohydrates such as dextran, cellulose and nitrocellulose, plastics such as polystyrene, polycarbonate, polypropylene and polyamide, inorganic substrates such as glass, silica gel and aluminum oxide, and high molecular weight cross-linked proteins. Plastics are optionally plasma-treated to improve binding and may be masked during plasma treatment to localize binding sites in the test field. Immunosorbent materials may be fabricated and used in the form of particles, beads, mats, sponges, filters, fibers, plates, and the like.

"Immobilize": Assays are built up from reagents that are soluble or are solubilized upon rehydration in the test sample, a diluent, or in another reagent, and from reagents that serve to capture and concentrate the analyte at a defined location or surface in the device. The terms "immobilize" or "immobilized" as used herein indicate that test analyte and affinity capture reagent binding is in effect irreversible under conditions of the assay.

"Agglutination" refers to a class of analyte:affinity capture molecular binding interactions characterized by formation of colloidal flocs or macroscopic aggregates. When antibodies are the capture molecules, such antibodies are termed agglutinins Precipitins also produce agglutination-like reactions with particles.

"Endpoint" is used here as shorthand for a "result" from either qualitative or quantitative assays, and may refer to both stable endpoints where a constant activity or level is attained, and to rate reactions, where the slope of a reactant or product concentration as a function of time is monitored continuously.

"Microfluidic device" is a hydraulic device, cartridge or card with at least one internal channel, void or other structure having at least one dimension smaller than 500 microns, but in some cases twice that, as when the sample contains particles or a bead reagent is used. The devices described here may be hybrids of microfluidic and microscale fluid structures, but generally require small sample volumes less than 1 mL, more preferably less than 200 uL, and most preferably less than 50 uL. Microscale is taken to indicate an internal dimension less than 5 mm, but in most instances less than about 2 mm. On-board processing means for fluidic operations of pumping, diluting, concentrating, dissolving, diffusing, mixing, reacting, precipitating, adsorbing, filtering, lysing, separating, metering, heating, cooling, and condensing as are known in the art may be incorporated in the device. Microfluidic devices may be fabricated from various materials using techniques such as laser stenciling, embossing, stamping, injection molding, masking, etching, and three-dimensional soft lithography. Laminated microfluidic devices are further fabricated with adhesive interlayers or by thermal adhesiveless bonding techniques, such by pressure treatment of oriented polypropylene. Fabrication of injection molded microfluidic devices may include sonic welding or UV-curing glues for assembly of parts.

"Microfluidic channel", also termed "microchannel", means a fluid channel having variable length, but cross-sectional area often less than 500 μm, in some cases twice that, as when the sample contains particles or a bead reagent is used. Microfluidic fluid flow behavior in a microfluidic channel is highly non-ideal and laminar, as in Poiseuille flow, and may be more dependent on wall wetting properties and diameter than on pressure drop. Hybrid microscale and microfluidic devices are encompassed here. Microfluidic channel surfaces may be passivated if desired.

"Microfluidic valves" include hydraulic, mechanic, pneumatic, magnetic, and electrostatic actuator means with at least one dimension smaller than about 500 μm, in some cases twice that, as when the sample contains particles or a bead reagent is used. A representative flap valve of the genus is described in U.S. Pat. No. 6,431,212. One-way "check" valves are also known in the art and can be used to direct the flow of solubilized reagents and sample for microfluidic device-based assays. Ball pinch valves as described in U.S. Pat. No. 5,718,567, are also useful in the devices of the present invention, as may be the valves of U.S. Pat. No. 6,729,352.

"Microfluidic pumps" are inclusive of "microscale pumps", and include for example, bulbs, bellows, diaphragms, and bubble microactuators intended to force movement of fluids, where the structures of the pump are in fluidic connection with a microfluidic channel. Such structures include the mechanically actuated recirculating pumps described in U.S. Pat. No. 6,743,399 and U.S. Patent Application Publication No. 20050106066. Such pumps may be robotically operated on operated by hand. Electroosmotic pumps are also provided. Such pumps can be used in place of external drives to propulse the flow of solubilized reagents and sample in microfluidic device-based assays.

"Bellows Pump", in the pneumatic embodiment, is a device formed as a cavity, often cylindrical in shape, bisected in coronal section by an elastomeric diaphragm to form an "upper" (or first) and a "lower" (or second) half-chamber which are not fluidically connected. The diaphragm is controlled by a pneumatic pulse generator generally connected to the upper half-chamber. Positive pressure above the diaphragm distends it, displacing the contents of the second half-chamber, negative gauge pressure (suction) retracts it, expanding the second half-chamber and drawing fluid in. By half-chamber, it should be understood that the upper and lower half-chambers are roughly symmetrical or equal in volume above and below the diaphragm. The lower half-chamber is connected to a fluid in-port and out-port. The fluid in-port and out-port may be separate ports or a single port. As described above, a pneumatic pulse generator is pneumatically connected to the upper half-chamber, generally by a microchannel, which is valved. In the complete apparatus, pneumatic actuation is programmable. Thus, programmable pneumatic pressure logic used by the pulse generator will actuate the diaphragm on signal and open and close valves on signal. When the pulse generator is off-cartridge, nipples or inlets, a pneumatic manifold and solenoid valves are provided to connect the card with the controller.

In use, fluid enters the lower half-chamber of a bellows pump through the inlet when negative pressure is applied to the diaphragm (or passively, when fluid is pushed in by a second bellows pump). Then, when positive pressure is applied to the diaphragm, during the downstroke, the fluid contents of the chamber are displaced out through the outlet. By supplying a train of positive and negative pressure pulses to a diaphragm, fluid can be moved in and out of a bellows pump chamber. This fluid motion becomes directional by the application of synchronized valve logic.

Pairs of bellows pumps, i.e., "dual bellows pumps", can mix fluids or suspensions when configured with a first diaphragm pressure-actuated and a second diaphragm passive so as to force reciprocating flow between the two bellows chambers. Reciprocating flow can also be obtained by synchronously actuating both diaphragms with alternating or inverted pneumatic pulses. Similarly, a multiplicity of bellows pumps can be fluidly connected in series to perform a mixing function. Note that a manual embodiment is obtained by joining the flexible membrane to the cover over the bellows pump chamber, so that the flexible cover can be simply pressed with a thumb or finger in order to expel fluid from the bellows chamber, and that pairs of bellows pumps, manually operated as described, can be used to pump fluid back and forth through a central chamber or channel with eductive mixing as described and embodied here.

"Self-priming" connotes a microfluidic channel that is fabricated from a material or is treated so that the channel is wettable and capillary flow begins generally without the need to prime the channel.

"Via" refers to a step in a microfluidic channel through a layer, most characteristic of laminated devices built from sheets or rolls, but may also be found in molded devices with multiple layers.

"Isolation" or "isolated" refers to a system of seals and enclosures that protect the user from exposure to clinical materials potentially contaminated with an infectious agent, toxin or unknown biohazard. For example, a single-entry device may optionally include a flexible bung which is self-sealing following withdrawal of the sample dispensing device. Isolation microfluidic devices may also include vent filters and any on-board "reagent-", "waste-" or "rinse pack" sealingly enclosed within the device. Medical isolation is commonly further characterized as "reverse isolation" or "forward isolation", as would be known by those skilled in the art. Exposure may occur if the operator of the device is contacted by the sample; contamination of the sample may occur if the sample is contacted by the operator, or by a fomite, or by another sample.

"Single entry" devices are disposable, and intended for single use. Generally, one sample per device is applied, the device is then sealed, and the assay performed. Swab capture devices are a means for sanitary sample capture in which the swab to be analyzed is inserted into the device and the handle is broken off so that the swab becomes sealed inside the device. Closures in which blood, plasma or other bodily fluid, or lavages, is taken up in the device by pipetting, by aspiration or by capillary action and the orifice then sealed are also recognized here as single-entry means.

"Waste pack" is a cavity or reservoir that serves as a receptacle for discharged sample, rinse solution, and waste reagents. Typically, a waste pack also includes an absorbent pad, for example consisting of a fibrous bat with or without a hydrophilic polymer, and includes absorbent foams; absorbent sponges; superabsorbent polymers; or absorbent gelling materials. The absorbent pad is a commonly a bibulous material and also can be used to propulse fluid flow by capillary wetting in place of, or in concert with, microfluidic pumps. Other materials include papers, sponges, diaper materials, Contec-Wipe™ (Contec, Spartanburg S.C. USA), for example.

In a preferred embodiment, waste packs may be used to contain biohazardous material by incorporating a flexible or elastomeric film or membrane sealingly attached to the body of the microfluidic device and enclosing the waste pack, which contains an absorbent bat, in a waste chamber inside the device body. The membrane stretches as the bibulous material expands. The cavity outside the isolation layer is vented to atmosphere, but the membrane ensures that waste material is contained and isolated. The bibulous material may be pre-treated to comprise a disinfectant as an added precaution.

"Vent" refers to a pore intercommunicating between an internal cavity and the atmosphere. An isolation vent further is fabricated of a housing containing a membrane composition that is selected to prevent transit of fluids but is permeable to gas, thus forming a liquid barrier. An example is Mupor™ a porous PTFE composition available from Porex Porous Products Group (Fairburn Ga., USA).

"Test field" refers to the site or zone in a microfluidic device-based assay where the assay endpoint is observed or measured. A preferred test field is, for example, an optical window in the coverplate of the device, optionally equipped with a magnifying lens.

"Means for isolation" include impermeable cartridge body, gas permeable hydrophobic venting, bibulous padding in waste chamber, disinfectant in waste chamber, elastomeric membrane separating pneumatic actuator from blister pack, flexible membrane separating bibulous padding from vent, valve with elastomeric membrane actuated by suction pressure, suction pressure in said sample entry port, on-board reagent pack, single-entry sample port, and disposable device, among others.

"Means for detecting" as used herein refers to a device for assessing and displaying an endpoint, i.e., the result of an assay, and may include a detection channel and test pads. Detection endpoints are evaluated by an observer visually in a test field, or by a machine equipped with a spectrophotometer, fluorometer, luminometer, photomultiplier tube, photodiode, nephlometer, photon counter, voltmeter, ammeter, pH meter, capacitative sensor, radio-frequency transmitter, magnetoresistometer, or Hall-effect device. Particles, beads and microspheres, impregnated with color or having a higher diffraction index, may be used to facilitate visual or machine-enhanced detection of an assay endpoint. Magnifying lenses in the cover plate, optical filters, colored fluids and labeling may be used to improve detection and interpretation of assay results. Means for detection of particles, beads and microspheres may include "labels" or "tags" such as, but not limited to, dyes such as chromophores and fluorophores; FRET probes (including those known as "Molecular Beacons"), enzyme-linked antibodies and their chromogenic substrates, radio frequency tags, plasmon resonance, or magnetic moment as are known in the prior art. Colloidal particles with unique chromogenic signatures depending on their self-association are also anticipated to provide detectable endpoints.

QDots, such as CdSe coated with ZnS, decorated on magnetic beads, or amalgamations of QDots and paramagnetic $Fe_3O_4$ microparticles, optionally in a sol gel microparticulate matrix or prepared in a reverse emulsion, are a convenient method of improving the sensitivity of an assay of the present invention, thereby permitting smaller test pads and larger arrays. Fluorescence quenching assays are anticipated. A variety of substrate and product chromophores associated with enzyme-linked immunoassays are also well known in the art and provide a means for amplifying a detection signal so as to improve the sensitivity of the assay. Detection systems are optionally qualitative, quantitative or semi-quantitative.

"Target Biomarkers": Those skilled in immunology are familiar with ELISA and agglutination assays. Targets for microfluidic detection assays include diagnostic biomarkers useful in the practice of internal medicine. Classes of biomarkers suitable for ELISA are well-known in the art and include proteins and peptides associated with pathology, hormones, tissue and coagulation factors, and small molecules, etc. These would include cancer markers associated with bladder, prostate, breast or lung cancer, for example, and also blood group antigens and antibodies useful for testing cross-match compatibility.

Targets also include infectious and parasitic agents. In the early and acute phase of an infection, laboratory diagnosis tends to rely on direct detection of the invading pathogen. This may involve in vitro culture or microscopic examination of test specimens. Test tube and microtiter plate-formatted serological methods are also useful. Non-specific assays such as cold-agglutinins or sedimention rate of whole blood are also used to support the clinical impression. Definitive laboratory tests rely extensively on live culture. But for a number of reasons, this is not fully satisfactory. Culture methods are plagued by delays, sample contamination, false negatives, and in the case of emerging diseases, by lack of reliable growth substrates and protocols for culture of viable organisms. Some well known but very fastidious pathogens are also not routinely cultured.

In particular, time to culture is unsatisfactory. Blood cultures are typically, for example, not read for 14 to 20 hours, and a positive culture, indicated by turbidity in liquid broth, must be followed by isolation of the causative organism on solid media, identification by biochemical tests, with subsequent antibiotic susceptibility testing. Cultures for tuberculosis typically are read 3-6 weeks after inoculation. Viral culture, which relies on cell and tissue culture, or inoculation of egg chorioallantoic membrane, takes one to fourteen days and is difficult at best. Detection of protozoan parasites generally relies on microscopic observations or serodiagnosis, tests that are not generally available outside of specialized clinical laboratories. In vitro testing and sample handling is also inherently unsafe and can contribute to iatrogenic infections.

Therefore, there has been substantial interest in developing laboratory diagnostic tests based on biomarkers developed from the genome, proteome, or metabolome of known and emerging pathogens, particularly tests that minimize sample handling and that provide results in real time or near real time at the point of care.

The range of needed assays can be grasped from the following partial list of known pathogens, which must be differentiated from closely related microbial normal flora and environmental contaminants.

Airborne respiratory pathogens include, for example, *Streptococcus pneumoniae, Streptococcus pyogenes, Mycoplasma pneumoniae, Klebsiella pneumoniae, Mycobacterium tuberculosis, Bordatella pertussis, Legionella pneumophila, Corynebacterium diptheriae, Hemophilus influenza, Chlamydia pneumoniae, Varicella* virus, Measles virus, Mumps virus, Respiratory Syncytial Virus, Coronavirus, Rubella virus, Influenza virus, including hemaglutinin group H1-5, Adenovirus and *Pneumocystis carneii*, among others, and for which serodiagnosis is feasible.

Food and water-borne enteric pathogens include, for example, *Salmonella typhosa, Salmonella enteridis, Salmonella cholerasuis, Salmonella typhimurium, Shigella dysenteri, Campylobacter jejuni, Vibrio cholera, Helicobacter pylori, Escherichia coli* (strains producing heat stable or heat labile enterotoxin, such as serotype O157:H7), *Clostridium botulinum* as a source of toxin, *Clostridium perfringens, Listeria monocytogenes*, Polio virus, and Hepatitis virus A and B, *Entamoeba histolytic, Schistosoma mansoni, Clonorchis sinensis, Trichinella spiralis*, for example.

Blood-borne pathogens include, for example, *Salmonella typhosa, Salmonella paratyphi, Bacillus anthracis, Brucella abortus, Brucella suis, Brucella melitensis, Yersinia (Pasteurella) pestis, Pasteurella multocida, Francisella tularensis, Spirillum minus, Burkholderia mallei, Leptospirum ictoerohaemorrhagiae, Coxiella burnetii, Rickettsia typhi*, Hantavirus, Dengue fever virus, Yellow fever virus (and other viruses of the Flavivirus group), West nile virus, Japanese B encephalitis virus, St Louis encephalitis, Western equine encephalitis, Human immunodeficiency virus 1 and 2, Human T-cell leukemia virus 1 and 2, *Dirofilaria immitis* in dogs, *Plasmodium vivax, falciparum*, malaria, *ovale* and *berghei* to name a few.

Sexually transmitted diseases include, for example, Syphilis (*Treponema pallidum*), *Neisseria gonorrhoeae*, *Chlamydia trachomatis*, Human Immunodeficiency virus, Papilloma virus, Herpes simplex and also *Candida albicans*, an ascomycete.

Wound and bite pathogens include, for example, *Staphylococcus aureus*, *Streptococcus pyogenes* serotypes responsible for necrotizing fasciitis, *Pseudomonas aeruginosa*, *Clostridium perfringens*, *Clostridium tetani*, *Yersinia pestis*, *Bacillus anthracis*, and *Bacteroides fragilis*. Infections resulting from bites by mosquitoes, ticks, fleas and other arthropods generally are classified as blood-borne infections.

Central nervous system and CSF pathogens include, for example, *Neisseria meningitides*, *Streptococcus pneumoniae*, *Listeria monocytogenes*, syphilis, *Haemophilus influenza* serotype B, *Acinetobacter* spp, *Escherichia coli*, *Enterobacter* spp, *Pseudomonas aeruginosa*, *Staphylococcus aureus*, viral encephalitis such as Japanese B encephalitis, Mumps virus, Polio virus, herpes viruses (HSV-1, HSV-2), varicella zoster virus, and Rabies virus, and so forth.

Representative urinary pathogens are dominated by gram negative rods, and include, for example, *Proteus mirabilis*, *Proteus vulgaris*, *Escherichia coli*, *Klebsiella pneumoniae*, *Enterobacter cloacae*, and occasional *Pseudomonas* infections.

Normal flora of the respiratory tract include, for example, Streptococcal species, Corynebacteriaceae, and Neisseriaceae that must be differentiated from potential pathogens. Normal flora of the gastrointestinal tract include, for example, *Methanobrevibacter smithii*, *Bifidobacterium longum*, *Streptococcus faecalis*, Firmicutes, including Clostridia and Faecalibacteria, Lactobacillaceae, Acinitobacteria, Proprionobacteriaceae, Bacteroidaceae, and Enterobacteriaceae, as well as unidentified archaebacterial groups and species.

Although some organisms, when found in certain test specimens, are conclusively pathogenic, pathogenicity is not absolutely black or white. For example, *Escherichia coli* is widely regarded as a non-pathogen, and is ubiquitous in the colon contents of humans. However, certain strains acquire a *Shigella*-like enterotoxin that can result in highly disabling dysentery. Therefore, mere speciation of an isolate can be misleading, and a more complete assessment of the virulence of any isolate requires an inventory of its capacity to be invasive, toxigenic, and to resist host defenses. Importantly, a large body of clinical experience has demonstrated that certain organisms are typically associated with disease, and that virulent organisms commonly produce an immune response. This is the basis of vaccination, and also of serodiagnosis. Thus the need for point of care immunodiagnostics.

Immunoassay-type solid phase affinity capture sites for a microfluidic device-based assays are optionally localized in a diagnostic card on the plane of a test field in the form of a pad, zone or site. The capture molecule selected for the assay is adsorbed or crosslinked to the solid support matrix by methods known in the art. Support substrates include filter pads, sponges, beads, membranes, plastics, and other solids. In some instances the analyte may be coupled chemically or non-covalently to the solid phase and in others it may be incorporated into a material to be coated onto the solid surface. Solid substrates of this type are used in the same manner as for dipstick technology, an analogous art. In a microfluidic card for manual use, an optical window is typically provided with a view of the test site.

Solid supports are sometimes composed of a porous material, with pore sizes available range from 0.1 micron to about 250 microns, and may include depth filters, where pore size varies with depth in the material. Such solid supports are generally hydrophilic to ensure wettability or are treated to be hydrophilic. Bibulous materials, i.e., those absorbing aqueous solutions by capillary action, are well known in the art. Such materials include natural polymeric materials such as cellulosic materials (for example cotton, filter paper, chromatographic paper, nitrocellulose and cellulose acetate), agarose and crosslinked dextrans; but also include inorganic powders or fibers such as glass, silica gel, derivatized silica, diatomaceous earth, aluminum oxide; synthetic polymers such as polyethersulfones, polyesters, poly(vinyl chloride), vinyl chloride-propylene copolymer, vinyl chloride-vinyl acetate copolymer, polyacrylamides, polyacrylates, polyamides, nylons for example, wettable polyvinylidene fluoride (PVDF), either used as supplied or in composites with other materials; and ceramic materials or exploded metals. However, the solid support should not interfere with the detection signal. The porous material is typically attached to rigid or semi-rigid backing.

The porous material may be polyfunctional or be capable of being polyfunctionalized to enable covalent bonding of the capture molecule, for example with an aldehyde or with osmium tetroxide. Capture molecules may also be immobilized by non-covalent forces. Drying is often used as a means of "fixing" biological molecules to a surface-active solid support.

Solid phase substrates may also selected from plastic surfaces. Plastic surfaces such as polystyrene, polycarbonate, polypropylene, polyethylene terephthalate (PET), and polyamide have a native surface activity and will tightly adsorb biological molecules, but may optionally be activated to increase the density and tightness of adsorption of the capture molecule by gas plasma treatment, typically an etching gas such as nitrogen, oxygen or air (corona treatment) in plasma form. These gases serve to derivatize the polymer backbones of the solid support, creating ionizable and reactive amine and nitro groups or hydroxyl and carboxyl groups respectively. Such activated surfaces may be derivatized with heterobifunctional linkers to aid in attachment of the capture molecule. Glutaraldehyde pretreatment of the plastic surfaces has also been used. In general, any method known in the art for attaching the capture molecule to the immunosorbent that results in a usable solid phase affinity capture complex may be used.

Masking is commonly used to define boundaries within which the capture molecule will be fixed to the plastic surface. Masking to mark out a test site aids in visual recognition of a positive assay and also in machine-aided image analysis of automated test results. Plastic surfaces may be passivated outside the defined boundaries of the mask, or in negative masking techniques, the plastic surface will be activated, such as by low pressure gas plasma treatment, where unmasked.

The above listed solid phase affinity capture materials may also be formed as microspheres, beads, platelets, and other particle shapes. Immunosorbent beads well known in the art include latex beads, agarose in bead form (such as Sepharose 4B-Pharmacia); dextran beads, crosslinked proteins prepared as microspheres, magnetic microspheres containing a ferrite core, and silicate microspheres containing fluorophores, quantum dots, or even radiofrequency tags, and modified on the surface to permit crosslinking Numerous forms of latex are prepared by emulsion techniques, and are available tagged with dyes, both fluorescent and colored, quantum dots. Antigens can be coupled to bifluorescent beads such as those provided by Luminex Corporation (Austin Tex., USA) by a two-step carbodiimide process. Sedimentation of beads in microfluidic device-based assays has been described, and the size is typically optimized for the application. Thus beads can serve not only as solid phase supports for affinity capture, but also as indicator or labeling agents.

As a recent example of the state of the art, a synthetic matrix suitable for ELISA was created by copolymerizing plastic monomers with peptides consisting of the epitope site of nonstructural protein 1 of flavivirus, in this case Dengue Virus. These molecularly imprinted polymers, were then deposited on a solid underlayer (Dar-Fu Tai et al. "Artificial Receptors in Serologic Tests for the Early Diagnosis of Dengue Virus Infection" Clinical Chemistry 10:1373 (2006)). This solid phase affinity capture material performed very well in detecting seropositive sera supplied by the CDC.

Blocking agents, in particular certain detergents and proteins, weaken non-specific interactive forces that contribute to high background signals in ELISA. Blocking agents include bovine serum albumin, optionally methylated or succinylated, whole normal serum, such as horse serum or fetal calf serum, and other commercially available proteins such as casein, gelatin and non-fat dry milk.

Detergent-based blocking agents can also be used. The types of detergents which are appropriate are selected from nonionic, amphoteric, cationic, or anionic forms, and the selection is based on the nature of the solid surfaces being blocked. Considerations which govern the selection of the appropriate detergent blocking agent are well understood in the art. It is preferred to use detergents in combination with protein-based blocking agents. Suitable detergents which can be used either alone or in admixture with the protein blocking agents include polyoxyethylene sorbitan alcohol detergents (i.e., the Tween series), polyoxyethylene alcohols such as Nonidet P450 or polyoxyethylene ethers such as Triton X-100.

Referring now to the figures, FIG. 1 shows a microfluidic device for ELISA immunoassays. In this first embodiment, the device is constructed by a lamination process from layers of clear plastic such as polyethylene terephthalate (PET), polystyrene, polycarbonates, polyacrylates, or polyesters in general, joined by interposed layers of adhesive. Microchannels, voids and holes are first machined from the plastic layers and adhesive before assembly, so that a microfluidic network is formed. Alternatively, the device may be constructed by injection molding of a cover and base layer, optionally with interposed plastic layers of increasing complexity, the layers held together with adhesive or fused under pressure with heat or solvent.

Shown in FIG. 1 is a simple card 1 for immunoassay development. The card body is plastic and has coverplate 14 and baseplate (not shown). A schematic representation of the device ports and underlying microfluidic channels, reservoirs and structures is shown. Flexible layers 12 and 13 cover the fluid chambers of bellows pumps 4 and 8 and may be elastically deformed so as to propel fluid from one reservoir to the other and back in a reciprocal motion. The device is backed by a rigid sheet of material (not shown) so that all internal cavities are sealed.

In operation, sample port 2, via microchannel 3, is used to introduce test sample into the reservoir of left bellows pump 4. Similarly, "waste" port 9, via microchannel 10, is used to introduce and discard reagent solutions into and out of the fluid chambers of right bellows pump 8. Ports 2 and 9 extend through the device cover 14 and are continuous with the fluid chambers of bellows pumps 4 and 8. Microchannels 3 and 10 may be modified to include valves (not shown).

Active reciprocal flow of fluid between the right and left reservoirs is conducted through assay chamber 5 via focusing apertures 6 and 7. Note that a vent is not required for actual operation of the dual pump device because the displacement of fluid from one chamber during the pump downstroke is balanced by displacement of fluid into the other, the flexible membrane being compliant in both up and down directions. Assay chamber 5 is fully sealed and contains test field 11. Test field 11 is coated with immobilized affinity capture molecule.

Prior to assembly, reagents can be applied in or on microfluidic channels and test fields in a variety of ways. Various "printing" techniques are suitable for application of liquid reagents to layers of the device, e.g., micro-syringes, pens using metered pumps, direct printing, ink-jet printing, airbrush, and contact (or filament) methods, and the layers or sheets are then assembled into the completed device. For operation of the fully assembled card, sample can be injected through a self-sealing bung, or pipetted or otherwise deposited into the device and sealed with a sanitary closure such as a cap, stopper, lid or tape. A pinch, ball, flap or peanut valve in the sample inlet port further seals the system. All such microfluidic cards are generally intended for single use followed by disposal.

Alternatively, the test sample may be mixed first with a detection antibody, and the mixture is then passed over the capture antibody on a solid phase matrix or test zone. After free detection antibody is rinsed away, color development indicates the presence of bound analyte-detection antibody complexes. U.S. Patent Application Publication No. 20060127886 teaches away from adding test sample directly to detection antibody. The ordinary person skilled in the art is familiar with ways in which the order of steps in an assay protocol may be varied.

"Indirect" ELISA is used to increase sensitivity. First introduced in U.S. Pat. No. 4,235,960, the indirect ELISA employs a bridging ligand which is applied to bound target analyte on the solid phase capture matrix and recognizes the target analyte. Bridging ligands, such as antibodies to immobilized antigen, build up the immunoprecipitin lattice at the site of analyte binding. After another wash, detection reagent is then applied. In a typical "indirect" ELISA test format, detection antibody is directed against the immunoglobin tails of the bridging antibody, not the analyte. Five-fold or more increases in the quantity of bound detection antibody can be achieved. After final wash series, addition of color reagent results in a strong signal even in the presence of relatively low concentrations of analyte.

The "indirect" ELISA format has another advantage. Any number of target analytes, each forming complexes with bridging antibodies on physically separate test zones, can be detected with a common, or universal, detecting antibody.

In FIG. 2, we show that an affinity capture solid phase matrix can be subdivided into smaller zones and pretreated with separate affinity capture molecules for capture and analysis of multiple analytes. For example, a test strip composed of a row of five test field zones, as bands, strips, or spots, each embodying a unique reagent, provides a plurality of affinity capture matrices for simultaneous assay of five analytes. Means of applying affinity capture molecules includes the printing of bands, strips, or spots, for example with a dot-matrix printer or other dispenser (BioDot). Test fields may optionally be provided for control and validation of the assay. The zones may be laid down in unique shapes, for example a "plus" sign, a "minus" sign, or a "checkmark" to indicate their significance, and are typically labeled with instructions on a cover applied to the coverplate of the device or can be read by an instrument such as an optical scanner.

Shown in FIG. 2 is a microfluidic device 20 with coverplate 21 and baseplate (not shown) and a schematic representation of the device ports, chambers, and connecting microfluidic channels, reservoirs and structures. Flexible layers 22 and 23 cover the reservoirs of bellows pumps 24 and 25 and may be elastically deformed so as to propel fluid from one reservoir to the other and back in a reciprocal motion.

In operation, sample port 26, via microchannel 27, is used to introduce test sample into the fluid chamber of left bellows pump 24. Similarly, "waste" port 28, via microchannel 29, is used to introduce and discard reagent solutions into and out of the fluid chamber of right bellows pump 25. Ports 26 and 28 extend through the device cover 21 and are fluidly continuous with the fluid chamber of bellows pumps 24 and 25. Microchannels 27 and 29 may be modified to introduce valves (not shown), as may be useful in sanitary applications. The mixing embodiment shown here remains operable when all external vents are closed.

Active reciprocal flow of fluid between the right and left pump chambers is conducted through assay chamber 30 via focusing apertures 31 and 32. Assay chamber 30 is fully sealed and contains test strip 33. As illustrated in this embodiment, test strip 33 is coated with three species of immobilized affinity capture molecules in zones marked 34, 35, and 36 respectively. Assay chamber volume V 2 is typically equal to, greater than, or less than pump bellows chamber volume V1. An optical window typically overlies the assay chamber in these devices.

In this build, the test strip 33 and zones 34, 35 and 36, were prepared of PET plastic and negatively masked with an adhesive protective layer. The exposed plastic was then subjected to plasma etching under carbon dioxide (or argon) gas in order to derivatize the polymer backbones, which increases wetting and surface adsorption properties of the plastic. After application of the capture molecules in a coating buffer and drying, the mask is then removed and the plastic heated to 50-60° C. for a few minutes, optionally under vacuum or inert gas, to fix the molecules to the plastic. The test strip is then blocked with a blocking solution to eliminate nonspecific absorption of analyte or reagents and dried before assembly into the test cavity of the microfluidic device of FIG. 2.

Figure 2:
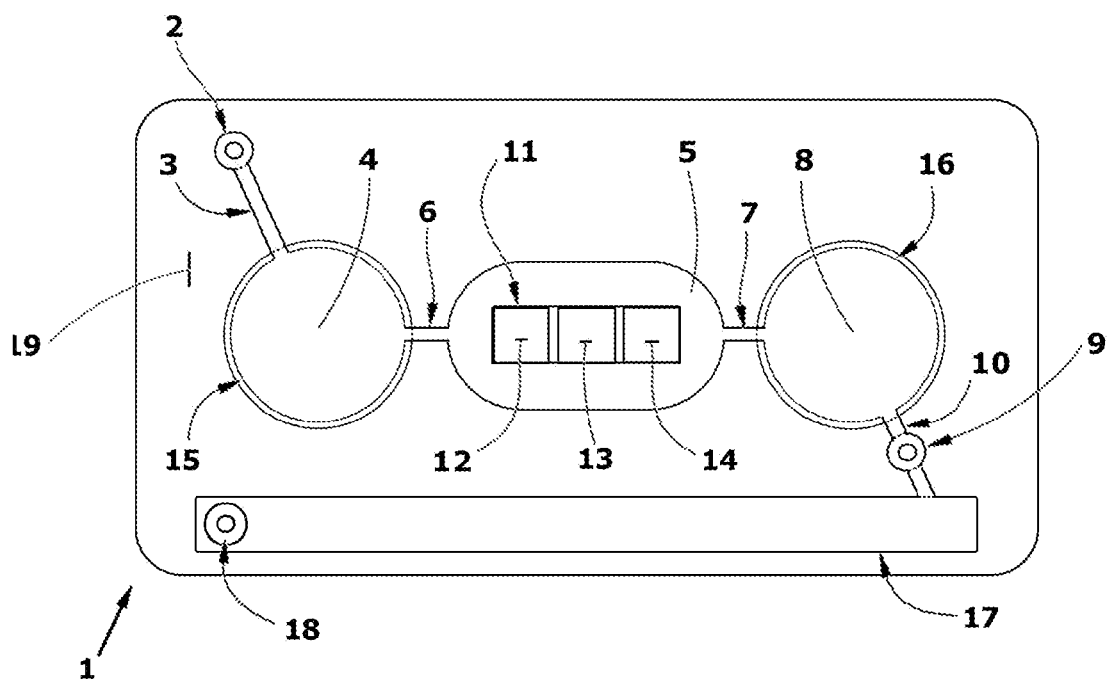
FIG. 2 illustrates a "test strip" mounted in a simple microfluidic card for immunoassay of multiple analytes from a single sample.

Devices may also contain an absorbent pad or bat 38, located for example in the waste reservoir 37 of FIG. 2. Absorbent pads or bats are used to retain discarded sample and reagents, and as is well known in the art, the absorbent may also assist in promoting directional capillary action. Examples of substances that may be used include cellulose, cellulose nitrate, cellulose acetate, glass fiber, nylon, polyelectrolyte ion exchange membrane, acrylic copolymer/nylon, Whatman 3M, polyethersulfone, 470 and 740-E from Schleicher and Schuell, (Keen, N.H. USA), or D28 from Whatman (Fairfield, N.J. USA), can be selected for their high fluid absorption and wicking speed. Waste receptacle 37 also includes a vent 39. Said vent may be formed from a housing containing an isolation filter or membrane that prevents transit of aqueous fluids but is permeable to gas, a useful sanitary measure.

Figure 3:
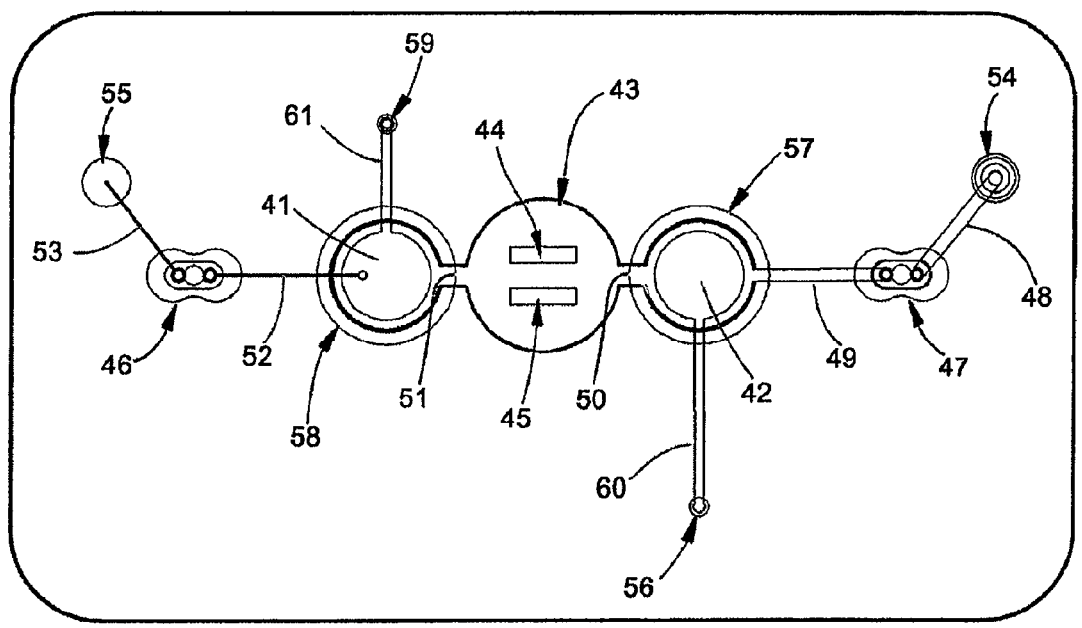
FIG. 3 is a schematic of a microfluidic immunoassay device with valves adapted for automated or semi-automated use.

FIG. 3 represents a schematic of a device 40 suitable for automation or semi-automation of an ELISA assay, or other heterogeneous binding immunoassay, in a microfluidics format. Analogously to FIGS. 1 and 2, right and left bellows pumps 41, 42 are used to power reciprocal fluid flow across assay chamber 43, shown here as containing two test fields (positive 44 and negative 45, see also FIG. 10) in which the appropriate capture molecules have been immobilized. Also shown are right and left valves 46, 47 controlling microfluidic channels 48, 49, 52, and 53 used in sample and reagent addition, mixing, rinsing, and in venting air during sample loading. Focusing apertures 50, 51 oppose each other as shown here, but may enter assay chamber 43 at angles off the center axis. Fluid port 54 is a sample inlet port; port 55 is an air vent fluidly connected with the sample inlet and is used to purge air from the system during sample loading, but is not necessary and can be closed for the micro-eductive mixing process. Port 55 may be replaced by a waste collection reservoir. Thus the fluid circuit is comprised of ports 54 and 55, channels 48, 49, 50, 51, 52, 53, fluid chambers of the bellows pumps 41, 42, and assay chamber 43. Pneumatic channels and air pressure ports off-card (not shown) are used to drive diaphragm 57 of bellows pump 42 and diaphragm 58 of bellows pump 41. Air vents 56, 59 equilibrate pressure above the diaphragm of bellows pumps 41, 42. Not shown is a waste reservoir. Pneumatic valves 46, 47, pumps 41, 42, pneumatic actuators, and waste structures of representative microfluidic devices 1, 20 and 40 are described in more detail in the following figures.

FIG. 4 shows a pneumatic "peanut" valve 70 schematically and its action is shown in cartoon form in FIGS. 5A and 5B (upper panel—valve open; lower panel—valve closed). In FIGS. 4 and 5A and 5 B, microfluidic channels 71, 72 entering from the right and upper left enter a microcavity 73 (100-500 microns in diameter) at two vias 74, 75 capped by a flexible polyurethane or PET diaphragm layer 76 that is laser welded to the plastic body 77 of the valve. An elastomer is preferred for the diaphragm. A third cavity 78, apposing the flexible layer, but located in a layer of the valve body above the fluid path, serves as a pneumatic actuator. Negative pressure (see FIGS. 5A and 5B), via control pneumatic actuator channel 79, pulls the flexible layer up and away from the step vias 74, 75 in the fluid path, opening a path for fluid to flow from the left to right microchannels 71, 72 as shown. Similarly, when positive air pressure is applied to the pneumatic actuator or control circuit, the valve is closed, blocking fluid flow. The pneumatic actuator circuit is also a microfluidic structure, and is built into the card. Valves 70 can be ganged or operated independently from positive and negative air pressure sources off-card. Generally this is handled by computer, but manual activation may also be used. This valve structure is used for stop flow in the Microflow microfluidics assay instrument (Micronics, Redmond Wash. USA). Note that the fluid path is isolated so that no user contact with the test fluids is possible following entry of the sample into the valve body and that the default position of a valve with elastomeric diaphragm is "closed".

Figure 1:
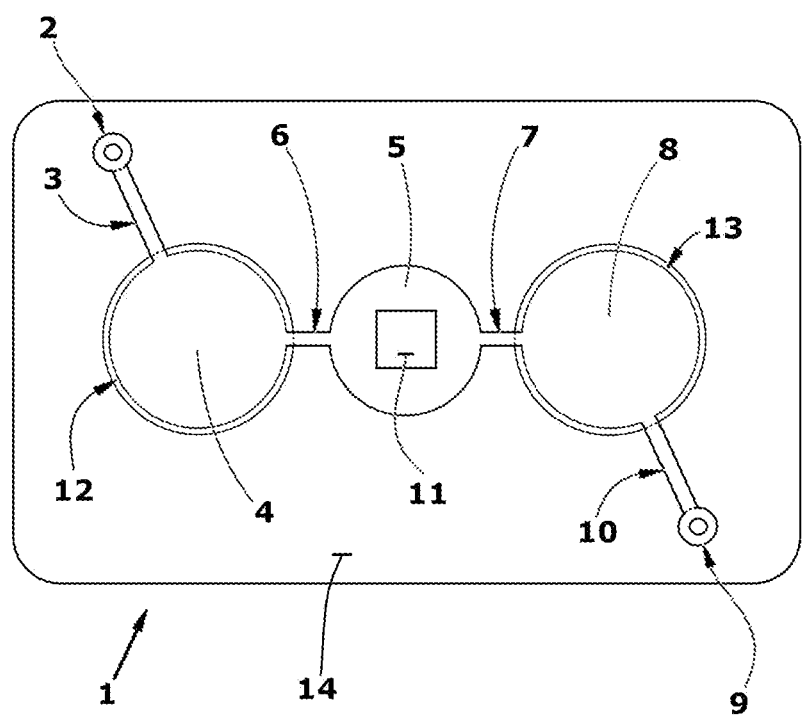
FIG. 1 illustrates an embodiment of a simple microfluidic card for immunoassay in a manual, automated or semi-automated format.
Figure 6:
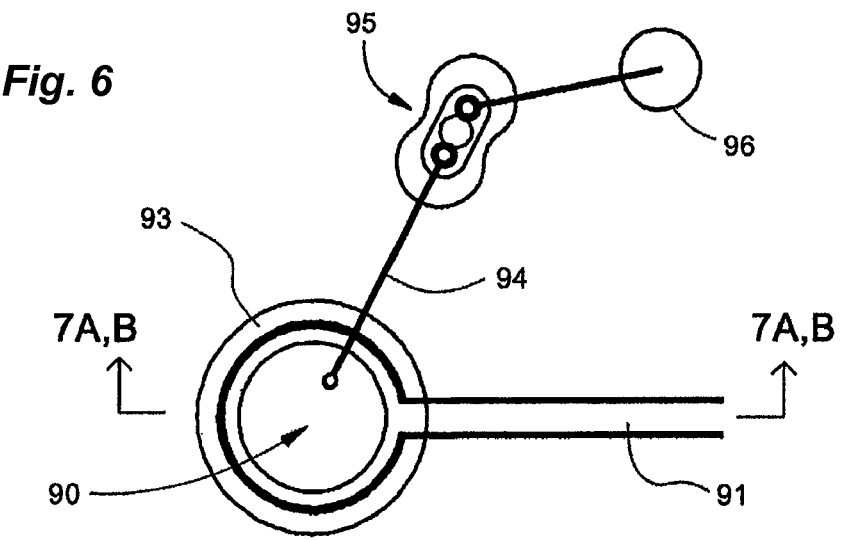
FIG. 6 is a plan view of a microfluidic "bellows pump" for fluid pumping and mixing.

FIG. 6 is plan view of a microfluidic bellows pump 90. The pump works analogously to a diaphragm pump as can be seen from FIGS. 7A and 7B. For reference, the pump cavity is divided into two approximately equal volume chambers, a "lower" half-chamber 97 and an "upper" half-chamber 98, the lower half-chamber 97 for containing fluid, and the upper half-chamber 98 for pneumatic actuation. "Upper" and "lower" chambers, of course, can be inverted or stood on end without limitation. At rest, bellows pump flexible diaphragm 93 bisects the pump cavity in a coronal plane. Flexible diaphragm 93 is optionally an elastomer. Fluid enters the lower half-chamber 97 of the pump cavity through microfluidic inlet channel 91 in the plastic body 92 when the flexible diaphragm 93 is pulled up by vacuum (or passively when primed with fluid under pressure) and exits when the flexible diaphragm 93 is pushed down by pneumatic pressure in upper half-chamber 98. Here, pneumatic actuator channel 94 connecting with upper half-chamber 98, valve 95, and pneumatic pressure source 96 are used to control the pump. Similarly, in a manual embodiment, when the enclosing flexible layer (top, bottom, or top and bottom of the card) is depressed (either by hand or by machine), fluid is displaced from the bellows reservoir and escapes through fluidly connected microchannels. When dual bellows pumps are placed in tandem as shown in FIGS. 1-3, thumb pressure alternated from one pump to the other will result in reciprocating flow. Check valves can be positioned in the microchannels on either side of a bellows pump to force directional flow. Alternatively, check valves may be used to fully seal the dual pump subassembly during eductive mixing. In eductive mixing, air pressure in actuator channel 94 of upper half-chamber 98 is pulsed, driving flexible diaphragm 93, which in turn drives fluid in the lower half-chamber 97. The mathematics of the operation are described in more detail in a simplified schematic in FIG. 9.

Bellows pump materials may be varied to select the required stiffness and elasticity. Elastic layers generate positive pressure when the pump surface is depressed and negative pressure when the surface is released. We have found that both positive and negative pressure-induced flows, away from or toward the bellows pump respectively, can be advantageously used in operation of microfluidic device based assays. Note again that the user is isolated from contact with the sample and reagent fluids.

In one embodiment, the microfluidic device is packaged in the form of a kit, and contains on-board reagents sufficient for analysis of a single clinical test specimen. Most preferably, these kit-packaged cards are single-entry (i.e., a single entry to introduce the sample is made) and the card is otherwise sealed and self-contained.

Figure 8A:
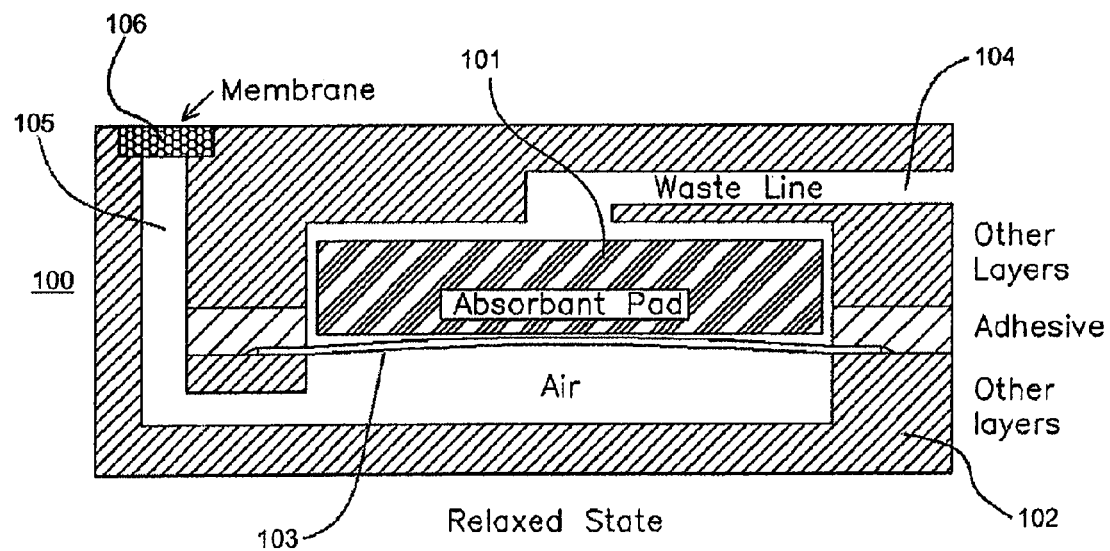
FIGS. 8A and 8B are sectional views of a microfluidic "waste pack" with an elastomeric inner sanitary isolation layer.
Figure 8B:
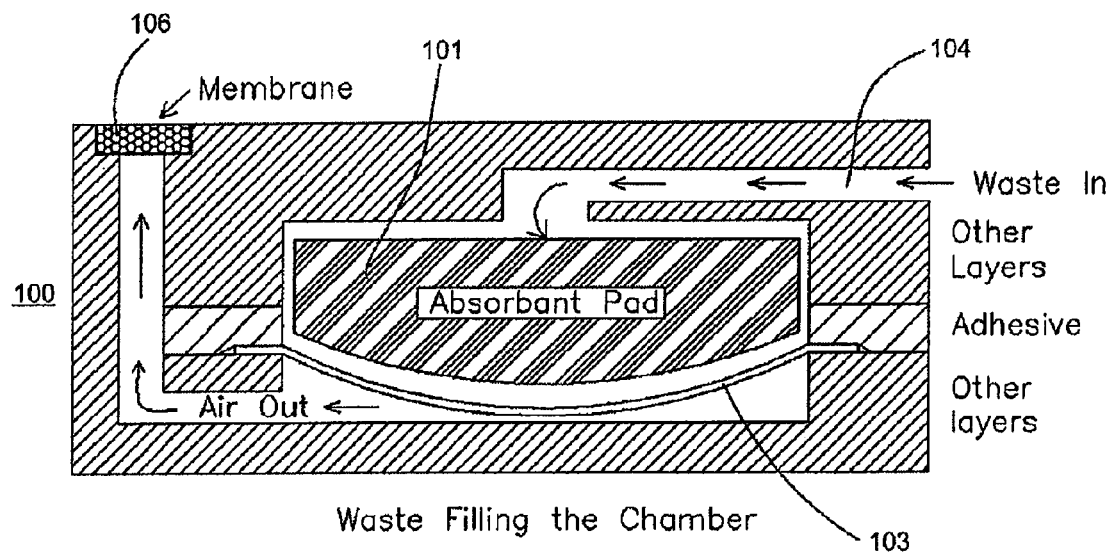

FIGS. 8A and 8B shows a cross-section through a waste receiving reservoir or apparatus 100 designed to prevent egress of contaminated sample and reagents from the microfluidic assay card. Waste entering through waste fluid channel 104 is imbibed into bibulous material (an absorbent pad or bat 101) positioned in the waste receiving reservoir in the plastic body of the card 102. The pad 101 swells as liquid is absorbed, as depicted in FIG. 8B. The waste receiving reservoir has a waste fluid channel aspect (here upper) and a vent aspect (here lower). Flexible or elastic film layer 103 separates the waste fluid channel aspect from the vent aspect of the waste receiving reservoir. A vent 105 is provided in the waste reservoir so that as the inner membrane expands, air pressure is equalized in the reservoir. Note that the vent may be supplied with a liquid barrier filter or membrane 106 to prevent egress of fluid as an additional safety measure. A flexible layer covering the waste receiving reservoir allows the reservoir to serve as a bellows pump.

Similarly, for reagent administration in a closed system, reagent is premeasured into a blister pouch in a sealed cavity on the card. In one embodiment for releasing the reagent when required, a sharp, positioned under the blister pouch, is contacted with the pouch when finger or mechanical pressure is applied to the opposing film, rupturing the pouch and releasing the contents. The chamber is fluidly joined with a microfluidic channel so that the reagent is simultaneously released and forced by the pressure through the device in the required direction.

Color development reagent, for example, or antibody reagents, may be safely stored in on-board blister pouches for use in the assay or added through a reagent port. By use of on-board blister pouches, the user is isolated from contact with biologicals or chemicals used in the assay.

Figure 9:
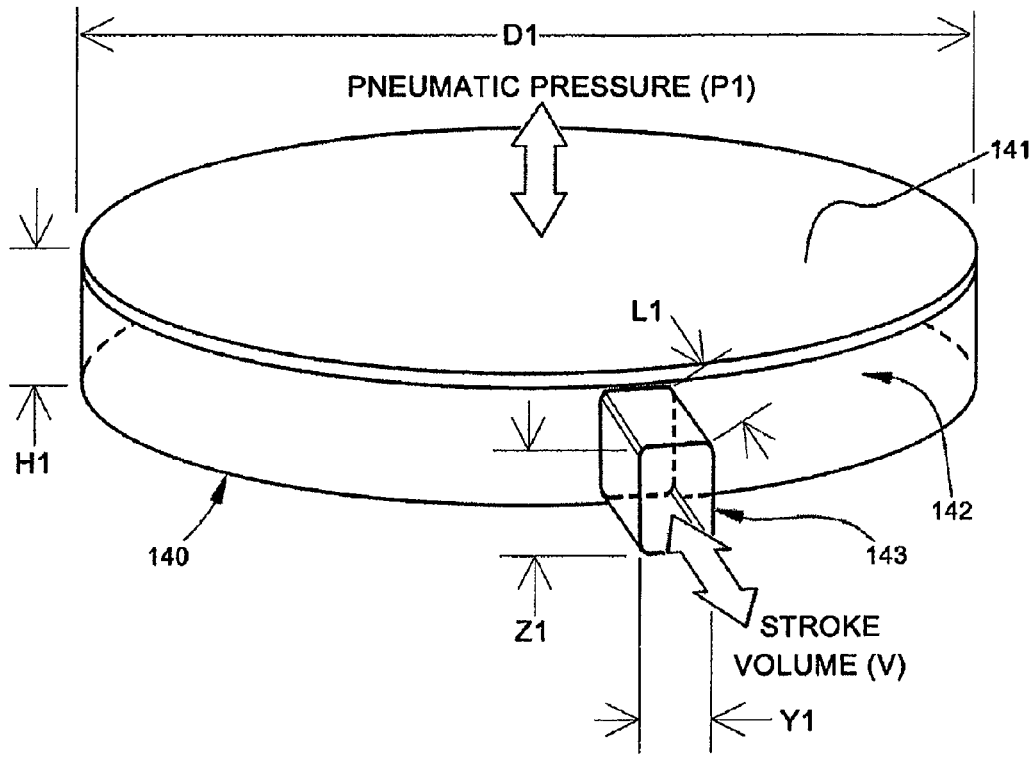
FIG. 9 is a conceptual model of a mixing aperture and bellows pump with representative dimensional and design considerations.

FIG. 9 demonstrates a "first cut" design calculation for eductive mixing. FIG. 9 is intended to be read with FIG. 7 and FIGS. 1, 2 and 3. FIG. 9 shows a lower bellows pump cavity 140, in explanation the "lower half-chamber" or fluid side of the pump. FIG. 7 shows a complete sectional view of a bellows pump with diaphragm 93 and both upper and lower half-chambers 97, 98. FIGS. 1-3 show how such bellows pumps 4, 8, 24, 25, 41, 42 are used in pairs.

Figure 7A:
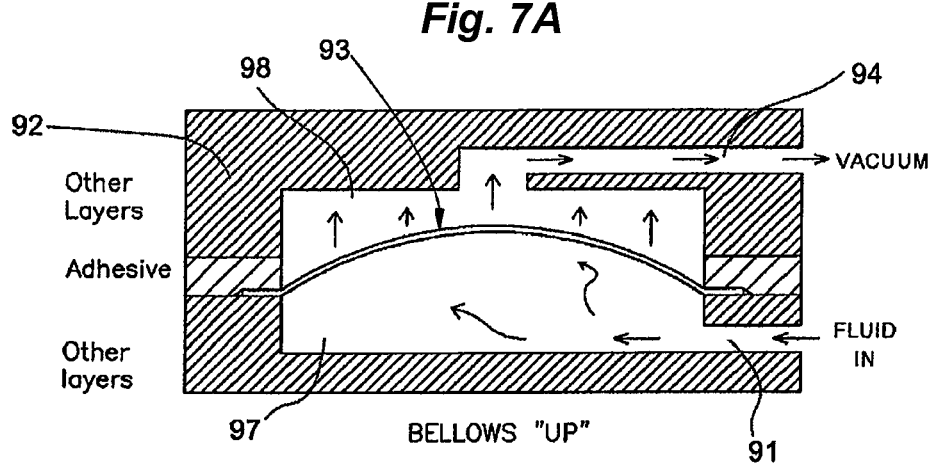
FIGS. 7A and 7B are sectional views of a microfluidic "bellows pump" for fluid pumping and mixing.
Figure 7B:
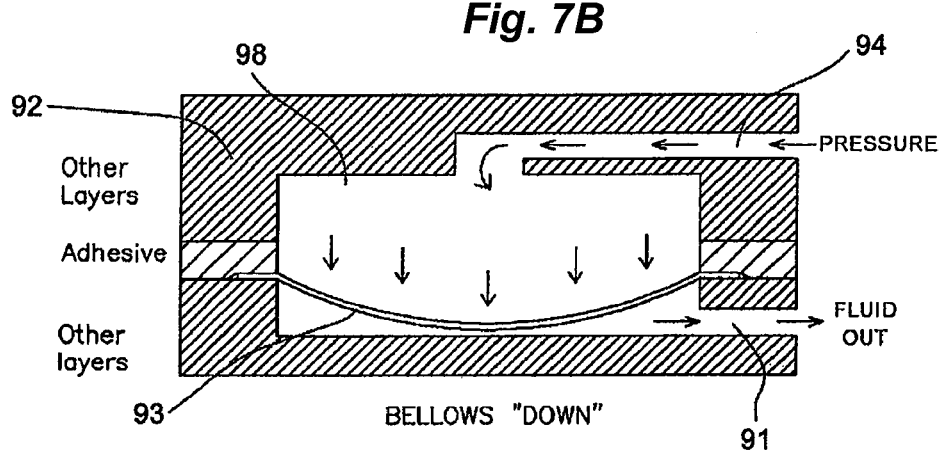

Now turning to FIG. 9, the lower half-chamber 140 of the bellows pump cavity is modeled as a cylinder with a flexible cover diaphragm 141, and with base and walls. The baseplate and coverplate 21 of the card body 20 are not shown here so that the internal fluid voids are more clearly represented. The upper half of the bellows pump cavity (see FIGS. 7A, 7B element 98) and pneumatic actuator circuit 94 are also not shown for clarity. The flexible cover diaphragm 141 must be compliant, as illustrated in FIG. 7, and is preferably elastic and durable. The cylinder has height H1, diameter D1, and nominal volume V1 142. The working diameter of the bellows diaphragm is an "effective diameter" based on compliance of the cover film and the pneumatic pressure, and therefore the actual displacement or "stroke" volume Vs of the flexible membrane from its resting to its fully compressed and extended position (convex deformation downward) is typically less than the nominal volume of the half-chamber V1 142 due to imperfect compliance and dead volume. Because pneumatic pressure is used instead of mechanical actuation, stroke volume is improved due to reduction of dead volume. The fractional effective fluid stroke volume (Vs/V1) of the pneumatically actuated bellows pump is greater than 0.5, preferably greater than 0.8. We also call attention to the active downstroke volume Vx, which is in fact may be greater than the displacement volume Vs because the stroke typically begins with the flexible cover distended (concave deformation upward) due to priming with fluid on the power stroke of the companion or tandem bellows pump, keeping in mind that these pumps are always used in pairs as shown in FIGS. 1-3. On the active power stroke of one diaphragm, the tandem diaphragm in the other chamber will become distended during its passive fill half cycle, and can then deliver a greater active stroke volume Vx on its power downstroke half cycle. Advantageously, Vx may be double Vs. The method of use involves depressing the flexible membrane of one pump, then the other, in alternation, so as to cause reciprocal flow back and forth through a central chamber separating the dual pump chambers. The total volume exchanged may be the sum of the active volumes of both pump chambers. In use, one pump is typically active and one passive during each half cycle, alternating in tandem, and thus further differentiating the mechanism from a pair of pump chambers in series. The pneumatic actuator may thus be directed to one of the two diaphragms, and the other diaphragm can be configured to follow passively, its upper half-chamber vented to atmosphere. Advantageously, the fluid systems can be completely closed during the mixing operation (i.e., without venting on the fluid side), a useful precaution against accidental operator exposure to the contents of the device and against formation of aerosols.

"Flow constrictive" or "flow focusing" aperture 143 has width Y1, depth Z1, and length L1. As shown, Y1 is a smaller than Z1, but this is not required. The purpose of the flow constriction is to accelerate the fluid in the aperture's cross sectional area so that the Poiseuille or parabolic flow regime characteristic of this scale of device is disrupted and microeddies, turbulence, and fluid jets form, emulating the action of a Penberthy eductor at a microscale. Mean velocities of 10-500 mm/sec are sought for immunoassay development as described here, and the aperture dimensions, active downstroke volume, and pressure pulse P1 on the flexible layer is configured to produce nominal average velocities in the range of 10 to 500 mm/sec, more preferably 20 to 200 mm/sec and most preferably 25-100 mm/sec, and increasing the apparent Reynold's number at the plume fringes.

These aperture dimensions and mixer conditions are configured to correspond to shear rates (flow linear velocity over dimension or diameter) in the range of 5 $\sec^{-1}$ to 500 $\sec^{-1}$.

Shear rates of up to 3000 sec$^{-1}$ are contemplated. Note that the shear rate may be calculated relative to Y as the critical dimension or Z as the critical dimension, where the critical dimension is generally the narrowest point of passage of the fluid and the flow velocity is determined by the pump chamber volume, diaphragm diameter D1 and stroke rate. The aperture may be generally rectangular in cross section, generally circular in cross section with diameter Y, or any convenient shape. Y may optionally equal Z; Z may optionally equal the height of the pump chamber H1. Aperture dimension L1 is generally selected to focus flow and is in the range of a few micrometers to a few millimeters. Ratios Z1/D1 and Y1/D1 are generally determined to be less than 0.5, more preferably less than 0.25, and preferably less than 0.1. Design optimization involves reducing both Y and Z while increasing stroke volume. Improved mixing characteristics are thus obtained by optimizing both the aperture and diaphragm configuration. A more complicated design calculation, also modeling viscosity, density and localized turbulent flow, may also be performed, or the design may be optimized empirically. Note that a critical lower limit in aperture dimension is crossed when wall shear results in destruction of assay targets or reagents, as is again best determined empirically. Secondary design considerations, generally optimized during assay development, include cycle time and duration of cycling, incubation temperature, pressure pulse interval and waveform, and pressure amplitude P1. Pressure pulses of 10 psig in the actuator channel (channel 94, upper half-chamber 98, FIG. 7B), with the tandem diaphragm operated passively on each half-stroke, were used in the examples presented here, but other pressures result in working embodiments also, for example a combination of positive pressure applied to one diaphragm while negative pressure is applied to the other. Pulse pressures in the range of about 0.1 Atm to about 5 Atm or higher are useful.

Figure 10:
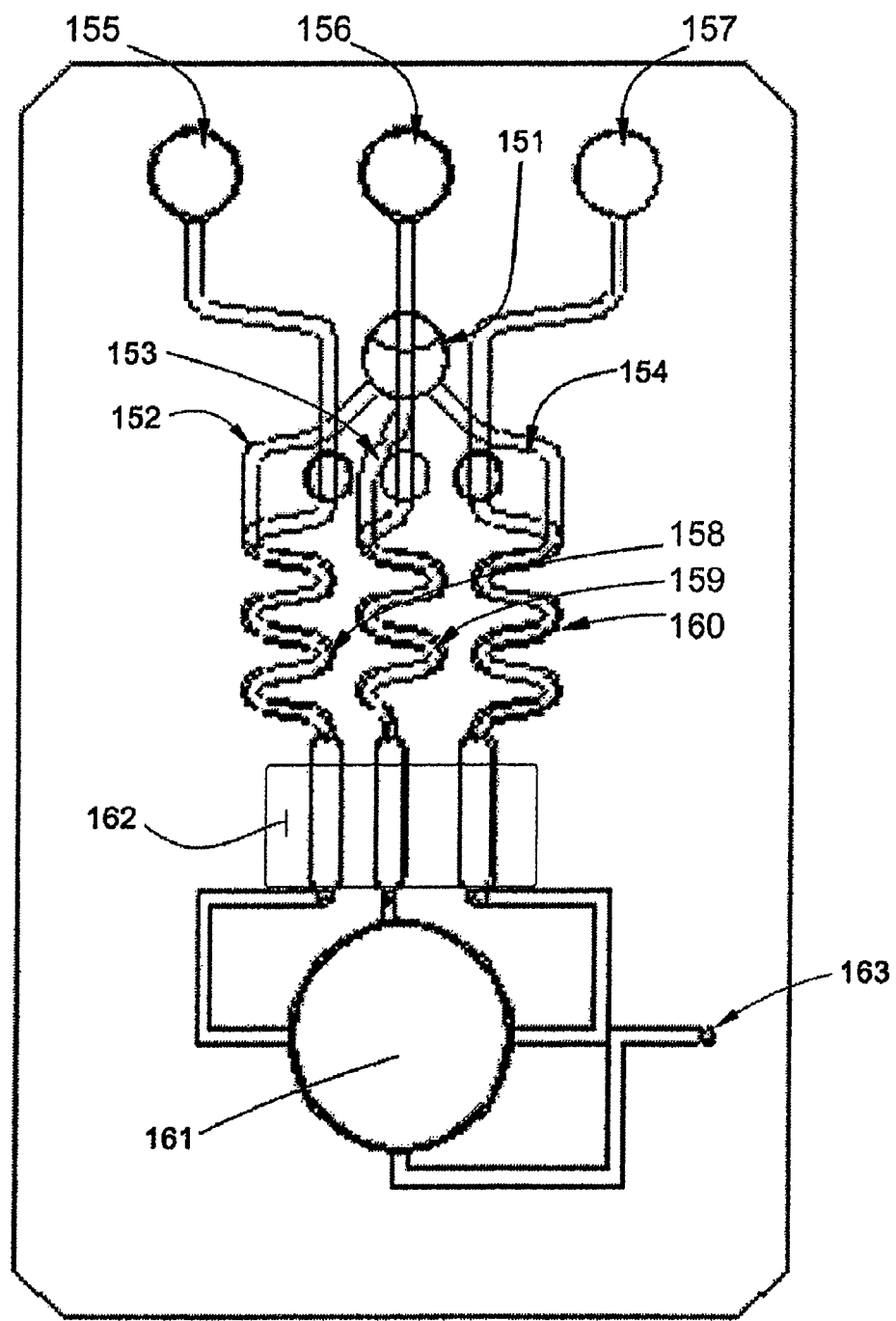
FIG. 10 is an embodiment of a microfluidic device for an agglutination assay.

Turning to FIG. 10, shown is a microfluidic card 150 for use in an agglutination assay. From a sample reservoir 151, three matching microfluidic channels distribute the sample fluid at a controlled rate into three channels of the assay 152, 153, 154. From reagent reservoirs at the top of the card 155, 156, 157, up to three reagents may be introduced into separate analytical channels. More or fewer channels may be used. The serpentine microchannels 158, 159, 160 are primed manually or mechanically with the bellows pump shown near the bottom of the card, which may also be a sealed waste reservoir 161, as described in FIG. 8. Vent 163 balances pressure in the waste reservoir. The vent 163 may contain a water impermeable:gas permeable filter barrier. The vent exit may also contain a valve (not shown) to assist in priming with bellows pump 161 fitted with an elastic cover layer in the coverplate. The results of the agglutination are read in a window for the test field 162 (see result in FIG. 12). Reagents with beads or cells coated with an affinity capture agent may be used to assist in detecting agglutination. Note that in an alternative configuration of an assay on the same card, a single reagent can be introduced into the "sample" reservoir and multiple samples can be introduced into the "reagent" reservoirs at the top of the card. Various permutations of the means and order of sample and reagent addition are easily contemplated. These agglutination assays may be used to diagnose infectious disease or to do crossmatches or to detect drugs.

Figure 11:
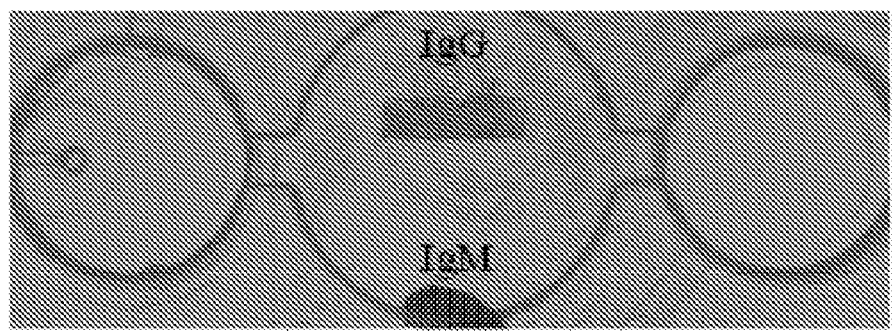
FIG. 11 is a photomicrograph of an assay chamber of the invention, showing the results of an assay of Example 2. A positive assay is indicated by a dark color characteristic of TMB precipitation in the test zone labelled IgG (upper bar).
Figure 12:
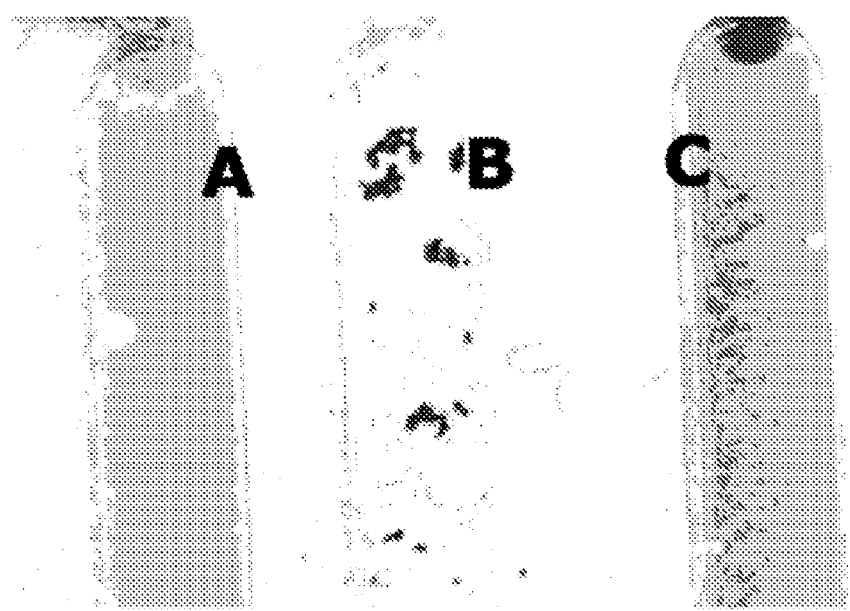
FIG. 12 is a photomicrograph showing the results of an agglutination reaction of Example 7.

FIGS. 11 and 12 are endpoint data for assays performed as described in the Examples discussed below.

Microfluidic channels built by layered sheet construction typically have square cross-sectional profiles. For reagents employing beads in agglutination reactions, the channel diameters are adjusted to permit passage of individual beads and bead agglomerates. Bead diameters are typically in the range of 1-100 microns, more preferably 2-15 microns (mean size) and the channel diameter must be sized accordingly.

Microchannels constructed of layers formed by extrusion molding may have more rounded channel profiles and a radius on each "via". The internal channel surfaces of injection molded parts are also somewhat smoother. The flow characteristics of the channels are significant because of the profound surface effects in the microflow regime. Surface tension and viscosity compound surface roughness effects. Channel surfaces may be passivated as required. The most narrow dimension of a channel has the most profound effect on flow. It follows that flow in channels that are based on square or circular cross-sectional profiles is controlled by the diameter or diagonal width, and design is typically varied to take advantage of this behavior. Reduction of taper in the direction of flow leads to a capillary effect for diameters below 200 microns. Conversely, opening up a channel to form a bulb stops flow unless pressure is applied. Vias in a channel can be designed to promote directional flow, a sort of solid state check valve.

Agglutination is a well known way of detecting an antigen:antibody reaction. Agglutination that is detectable by visible inspection is preferred. Of these visible means, colored microparticles, particularly what are known as "beads" in the art, are more preferred.

Colorable beads or particles and colorable latex beads are also known in the art and useful as detection means for immunoassays (see, for example, U.S. Pat. Nos. 4,373,932 and 4,837,168, both of which are incorporated herein by reference). Colored reagent solutions may also be used to enhance the visual characteristics of agglutination and aid interpretation. For visualization of agglutinations of very small particles, magnifying lens windows may be formed in the coverplate or faceplate of the device.

Optionally, beads may be "tagged" with labels to improve the sensitivity of detection. Fluorescent molecules, such as the rhodamine, fluorescein, or umbelliferone series, employed by themselves or with a quencher molecule, may be used (see, for example, U.S. Pat. Nos. 3,996,345 and 4,366,241, both of which are herein incorporated by reference). Chemiluminescent molecules, such as luminol, luciferin, lucigenin, or oxalyl chloride can be used as a signal means (see, for example, U.S. Pat. No. 4,104,029, herein incorporated by reference). Enzymatic systems that react with a colorless substrate to give a precipitated colored product, such as conjugated horseradish peroxidase with aminoethylcarbazole and hydrogen peroxide as substrate are also useful as signal means. Single and dual labeling may be used on a single bead species, or optionally, multiple bead species, each containing an individually recognizable signature of a combination of chromophores or fluorophores may be used.

Typically, it is desired to modify the surface of the particles in some manner so that they are more readily able to bind to the analyte. In such instances, the particles may be modified with certain specific affinity binding molecules to form conjugated particles. Immunoreactive affinity binding molecules include antigens, haptens, aptamers, antibodies (primary or secondary), and complexes thereof, including those formed by recombinant DNA methods, in hybridomas, or by peptide synthesis. Other common agglutination detection systems based on affinity capture include but are not limited to, biotin and avidin (or derivatives thereof), biotin and streptavidin, carbohydrates and lectins, effector and receptor molecules in general, and the nickel:histidine system.

The affinity capture molecule, for example an antigen or agglutinin antibody, may generally be attached to the bead using any of a variety of well-known techniques. For instance, covalent attachment of the specific binding members to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished.

The procedures for coupling enzymes to the present first members are well known in the art and are described, for example, in J. H. Kennedy et al., Clin. Chim Acta 70:1 (1976). Reagents used for this procedure include glutaraldehyde, p-toluene diisocyanate, various carbodiimide reagents, p-benzoquinone m-periodate, N,N-o-hexylenedimaleimide, heterobifunctional crosslinkers, and the like.

Alternative embodiments of the above mixing technology are also conceived. FIGS. 13A-B are a plan and cross-sectional view of a first apparatus for staining a glass slide, the apparatus having dual bellows pumps acting in tandem to produce reciprocating flow through a sealed reaction chamber formed on the face of the glass slide. FIG. 13C is a detail showing placement of the edge seal member.

By glass slide is indicated any of the generally planar substrate members as are commonly used for microscopy, including histopathology, oncology and cytology, for array hybridization, for proteomics, for high throughput screening, and so forth, without limitation.

In this illustrative example, the inventive apparatus 200 is formed on a baseplate 201, which may be built up from layers to enclose fluidic circuits or may be injection molded in one or more pieces. Generally the baseplate is made of plastic, although one may be machined from stainless steel, for example, if desired. A glass slide 202, with specimen(s) mounted thereon, is affixed to the baseplate using an edge gasket 203 as will be shown in FIGS. 13B and 13C in more detail. The specimens 204 in this illustration are on the underside of the glass surface. An aperture on the top web of the edge gasket defines an observation window 205 with viewing area 206 through the upper surface of the glass slide, as may be useful for photography or microscopy. A recess under the glass slide forms a sealed reaction chamber 207. An observation window may also be formed in the baseplate member for transmitting light through the reaction chamber.

A first bellows pump 212 and a second bellows pump 214 are used to propulse fluid back and forth through the sealed reaction chamber, as will be described in more detail below.

Turning to FIG. 13B, the glass side 202 is shown overlying a sealed reaction chamber 207 formed as a recess under the glass slide. The glass side rests in juxtaposition to a raised platform 208 defined by outside lateral walls 209 that join to the baseplate 201.

The recess is defined by inside lateral walls 210 and a slab 211 forming the floor of the recess. The slab may optionally be sloped or contoured and may be provided with a drain for draining fluid from the sealed reaction chamber 207. The sealed reaction chamber is a shallow tray extending across the area of the glass slide having specimens mounted thereon, where the depth of the tray is typically in the range of 5 to 100 micrometers.

Reagent fluid is forced from bellows pump 212 through a fluidic connection to the reaction chamber by a downward stroke of diaphragm 212a. Once air is purged from the internal hydraulics, fluid filling bellows pump 214 may be returned to bellows pump 212 by a downward stroke of diaphragm 214a. Valving is not shown for clarity. This process of sequential actuation of the diaphragms 212a and 214a may be repeated to generate a reciprocating flow between the tandem bellows pumps (212, 214) through the reaction chamber, thus ensuring that the specimens are fully contacted with the reagent fluid.

Because the dimensions of the reaction chamber are microfluidic in depth, mixing in the z-direction is primarily by diffusion, and is relatively rapid at depths of 5 to 100 micrometers. The pump action ensures that fluid in the chamber does not become locally depleted of reactants, fresh fluid is periodically washed through the chamber as required to complete the reaction of the reagent with the specimens. The "x" and "y" dimensions in the chamber may be configured to support high-throughput screening or smaller scale experiments as needed. If desired multiple copies of the apparatus 200 may be operated in tandem, either by hand or using an automated workstation.

For example, where specimens 204 are microarrays, probes may be introduced into the chamber to selectively bind with the arrays and then light up target molecules in the array. In other uses, where specimens 204 are tissue sections, stains or antibodies may be introduced into the chamber to selectively bind to certain cells, and those cells may then be visualized. In other instances, fluorescent probes are used, as in FISH (fluorescent in-situ hybridization), allowing researchers to track biological activities in situ. Similarly, sequencing reactions such as polony sequencing may be performed in chambers of this kind. The thickness of the viewing window may be selected as required to interface with an optical package, and image analysis is readily accomplished using digital pictures of the viewing area.

In this illustration, the edge gasket 203 is formed to enclose a lip 215 formed on the raised platform 206. This is shown in more detail in FIG. 13C. Slide 202 is sealedly clamped to lip 215 using gasket 203. Shown are outside lateral wall 209 of the raised platform and inside lateral wall 210 of the internal recess forming the sealed reaction chamber 207. Fluidic channel 216 formed between the outside lateral wall 209 and inside lateral wall 210 communicates fluidically between the bellows pump and fluid reagent reservoirs depicted in FIG. 13B and the sealed reaction chamber 207. Fluid entering the reaction chamber at 217 (FIG. 14) cannot escape unless provided with an exit or vent.

The edge gasket member is a formed article, generally a soft and pliant but tough material such as a silicone rubber or a vinyl rubber or other elastomer. In this gasket, a "u-shaped" trough extending the full internal edge of the gasket is slipped over the slide and lip 215 to make the seal. This simplifies the hydraulics and relieves bending of the slide as has been observed with other clamping systems, but requires facing the specimens downward into the reaction chamber.

If desired a rigid clamp can be affixed to reinforce the edge gasket 203 illustrated here. The rigid clamp will generally follow the shape of the edge gasket but be tightened over it the soft clamp if needed to prevent leaking of the reaction chamber under pressure. Other clamping systems may be used if desired.

Conveniently, heating devices or Peltier chips may be placed in the raised platform and temperature controlled within the reaction chamber. The effect of the heating devices is to control the temperature of the liquid, and advantageously the glass slide is not the conduit whereby heat is conveyed to the chamber, thus minimizing risk of damage to the specimens by overheating or freezing.

In a variant of this configuration, the sealed reaction chamber can be formed around a segment of a glass slide by inserting the slide through a slit or cutout on one end (or both ends) of the gasket. This is useful, for example, when labeling on a tab at one end of the slide is to be protected or when an electrical junction is required for mounting a wire harness to one end of the slide. The resulting electrical connection(s) may be useful for powering an electrode array in the reaction chamber or for operating a thermistor, while not limited thereto.

Surface tension within the reaction chamber is generally controlled by passivation or surfactants to facilitate wetting and to prevent bubble occlusion. Because the pumping action is robust, vertical orientation may also be used advantageously to remove bubbles during priming. A$CO_2$ flush has also been suggested to minimize bubble entrapment during wetout.

FIG. 14 is an exploded view of the apparatus of FIG. 13. Baseplate 201 supports a pair of bellows pumps 212, 214 for pumping fluid through reaction chamber 207, shown here exposed so that the recessed tray forming the bottom of the reaction chamber is readily observed. Fluid port 217 is representative of connections to fluidic circuitry embedded in the baseplate. The recessed tray may be sloped or graded to encourage draining of reagent fluids during rinsing cycles. The recessed tray may also contain heating or cooling elements if desired.

During assembly, the slide 202 is supported on the raised flat ledge 218 surrounding the recessed tray, and the edge walls are generally conformed dimensionally for a good fit. A guide lip may be used if needed so that the slide is readily registered on the platform top surface. The edge gasket 203 is the fitted around the edges of the slide and under outside lip 215 so as to seal the slide against the recessed tray, thereby forming a sealed reaction chamber 207.

By forming a hard support 218 for the slide member 202, the dimensional integrity of the reaction chamber is ensured. Soft sealing gaskets of the prior art are typically placed under the cover housing and compressed in place, a disadvantageous practice because the "z" dimension in the reaction chamber and the headspace volume cannot be precisely controlled, thus causing problems where the gasket is overcompressed or where the headspace is too large, which contributes to reagent wastage and also slows the diffusional component of the reaction rate by increasing the needed diffusional path lengths unnecessarily.

The reaction chamber is dissassemblable by reversing these steps, for example when it is desired to remove the slide for subsequent examination or archiving. Alternatively, the entire assembly can be archived as a single unit. The cylindrical housings of the diaphragm pump can be made to fit into mated recesses in the bottom of the base plate, permitting stacks of apparatus to be shelved.

The slide is commonly supplied by the end user and may be or not be supplied as part of the reactor apparatus.

FIG. 15 is a schematic view showing dual bellows pumps and fluid flows in the enclosed chamber. Arrows indicate reciprocating bidirectional flow. A downward stroke of the diaphragm of bellows pump 212 results in flow toward bellows pump 214. When a downward stroke of the diaphragm of bellows pump 214 is caused, flow returns in the direction of bellows pump 212.

A downward stroke of one bellows pump may be accompanied by an upward stroke of the opposing bellows pump, doubling the energy of the pumping action. Alternatively, a single pump may be actuated at a time, and the other pump slaved to the action of the active pump.

In a common routine, as typically executed under the control of a microprocessor-assisted apparatus, the pump strokes in each bellows pump are alternated from positive polarity to negative polarity. FIG. 16 is a plot showing alternating polarity of the strokes of a bellows pump diaphragm. The second bellows pump is operated in tandem by application of a synchronous inverted signal.

The signal may be pneumatic or electrical. Operation of pneumatic control systems has been described above. Electrical actuation of magnetically controllable or electrostatically controllable diaphragms is also known in the art and finds use in the diaphragm actuation systems of the invention.

As shown in FIG. 15, the diaphragm pumps may also be fluidically connected to external fluidic circuits, such as for pumping reagents from a fluid reservoir into the reaction chamber. Port 219 may connect to an external circuit or to a reagent reservoir.

FIGS. 17A-C are diagrams showing different configurations and the effect on fluid advancing through the sealed reaction chamber. An issue in microfluidic fluid systems is meniscus control during wetout. The balance of flow in these systems typically is described by a capillary component and a drag component as analyzed in co-assigned US Pat. Publ. No. US2010/0112723. Surface active agents, surface modification, geometry, and surface features are useful to control wetting. Vertical orientation of the apparatus so that the reaction chamber is primed from below is also useful in avoiding uneven wetout and residual entrapped bubbles. Advantageously, the devices, systems, and apparatus of the invention, unlike some prior art devices, may be operated in either the horizontal, vertical or inverted position.

FIGS. 18A-B diagrammatically represent different configurations of paired bellows pumps and flow patterns in the sealed reaction chamber. Thus the use of independently controllable pairs of bellows pumps provides a robust and flexible platform for mixing thin fluid layers having a microfluidic characteristic dimension.

In FIG. 18A, a system 220 with eight independently controllable bellows pump units 221 connected fluidically to sealed reaction chamber 207 having samples 204 disposed on a glass substrate are shown mounted in an integrated baseplate member 201.

FIG. 19 depicts yet another system 230 configured with ten paired bellows pumps for achieving coordinated complex mixing patterns so as to fully contact the specimens 204 with the fluid reagents of the process.

FIG. 20A is a schematic of multiple flows in a sealed reaction chamber. Flows are directed so as to produce overlapping fields of laminar flow that coalesce into a bulk flow from left to right in sealed reaction chamber 207.

FIG. 20B is an alternate form of an injector port 240 as may be supplied with tubulation for attachment to a bellows pump. Pulses of fluid entering the chamber 207 result in the fluid flow of FIG. 20A. Also shown is an alternate barb clamp system for use in sealing slide 202 over the chamber. In this case, the slide is upright in the chamber so that the specimens are bathed in fluid filling chamber 207.

FIGS. 21A-21F depict means for clamping, means for sealing, and means for releasing a cover plate of a sealed reaction chamber from a substantially planar substrate to which it is affixed.

Figure 21A:
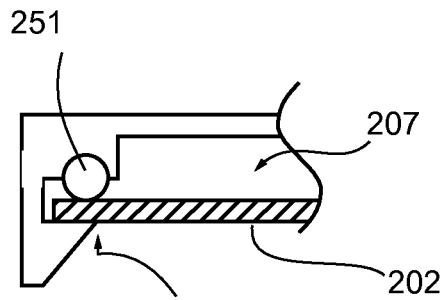

FIG. 21A illustrates an O-ring 251 inserted between a glass slide 202 and a coverplate for forming a sealed reaction chamber 207. A variety of compliant gasket materials known in the art may be used for internal seals.

Figure 21B:
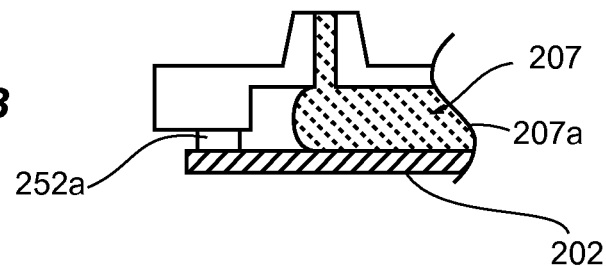

FIG. 21B depicts an adhesive seal strip 252a for forming a seal around a sealed reaction chamber 207 and slide 202. As shown here the chamber is filling with fluid 207a from an external port.

Figure 21C:
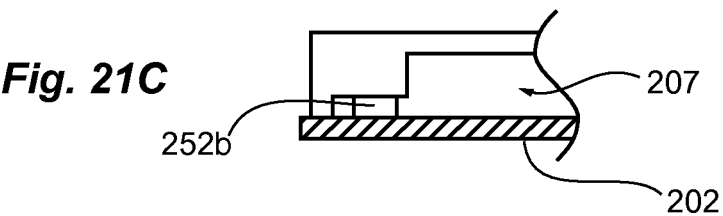

FIG. 21C depicts a second adhesive strip, where the dimensional geometry of the sealed reaction chamber 207 is ensured by a hard lip contacting the glass slide 202.

Figure 21D:
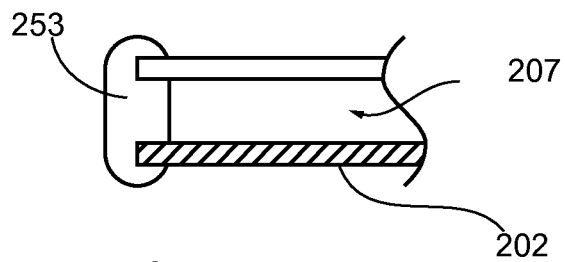

FIG. 21D depicts an end seal 253 formed of a compliant gasket material.

Figure 21E:
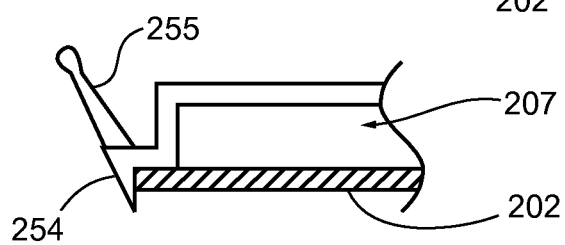

FIG. 21E shows a clamping feature 254 with release 255.

Figure 21F:
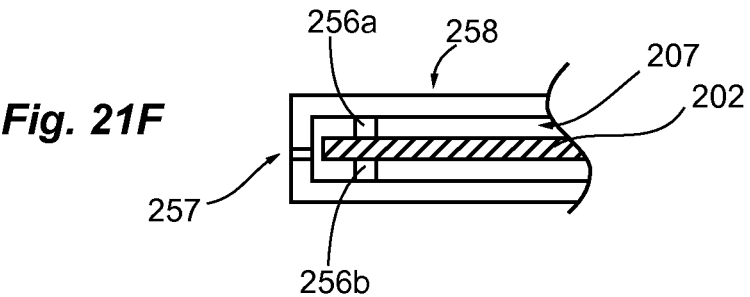

FIG. 21F shows a fully enclosing chamber for receiving a glass slide 202. Spacers 256a and 256b define a headspace volume 258 that contacts both the top and the bottom of the slide.

FIGS. 22A and 22B depict lip seals formed by micromolding of thermoplastics. The plastic lip yields under pressure to form a contact seal with the glass slide 202, thereby sealingly enclosing a reaction chamber 207.

Technologies illustrative of the art as generally known and which are incorporated herein by reference include U.S. Pat. No. 6,037,168 to Brown, U.S. Pat. No. 6,569,674 to McGarry, U.S. Pat. No. 6,773,677 to Thorne, U.S. Pat. No. 7,223,363 to McNeely, U.S. Pat. No. 7,235,400 to Adey, U.S. Pat. No. 7,318,913 to Loeffler, and U.S. Pat. No. 7,906,317 to Lee, for example.

Turning now to FIGS. 23A and 23B, shown is a representative embodiment 300 of the invention having a detachably insertable slide chamber minicassette and multiple reagent reservoirs with waste storage capacity on board.

In a first perspective view, the apparatus is seen to comprise a baseplate 301 module (also termed a microfluidic card) and a reversibly engageable slide chamber minicassette 302. Glass slide 303 is shown partially mounted in the minicassette subassembly 302.

In cutaway view (FIG. 23B), the glass slide 303 is shown to be angularly positioned for insertion into a latching barb mechanism 312 of the cassette housing 317. A compliant internal gasket 311 forms a seal around the sealed reaction chamber 310 when the slide is click locked in place. Reagent fluids are admitted through nipples 316a and 316b as described below. Other means for sealing and clamping, for example as described in FIGS. 21 and 22, may also be used.

Baseplate module 301 is comprised of dual bellows pumps (322, 324), reagent reservoirs or ports 307a-c, and waste fluid reservoir 304 with vent 308. The slide minicassette may be exchangeably plugged into docking bay 305 on the baseplate and moved from one baseplate to another if desired, for example if a complex reaction protocol is executed. The baseplate is loaded with reagents through reagent ports 307a through 307c, which are fluidly interconnected with the slide cassette via the bellows pumps and nipples 316a and 316b on the slide cassette, which sealedly engage ports 306a and 306b of the docking bay when the cassette is inserted.

Bellows pumps, as explained earlier, are used to provide the fluid motive force for loading reagents and for circulating fluids through the sealed reaction chamber 310. The bellows pump diaphragms 322a and 324a may be pneumatically actuated, or actuated electronically using solenoids or using electrostatic technologies known in the art.

While the microfluidic circuitry shown within the baseplate is made relatively simple for ease of explanation, more complex circuits may be formed by a process of laminating layers or by forming molded pieces with complex microfeatures and by a fusion process selected from solvent welding, ultrasonic welding, or laser welding as are known in the art.

The number of reagent reservoirs is sufficient, for example, for a three step staining protocol involving a staining step, a rinse step, and a counterstain step. More complex protocols can be performed with additional reagent reservoirs or with off-card reagents. The reagent reservoirs are also optionally removable, and may be provided with threaded nipples for insertion into connecting fluidic channels within the baseplate so that they may be exchanged at will. In one embodiment, baseplate modules and prefilled reagent reservoirs are sold separately, or in kits.

FIG. 24 is a cross-sectional view of the embodiment of FIG. 23. Slide minicassette subassembly 302 is shown in a partially open view. Slide 303 seals against housing 317 by a click lock clamp feature 312. A soft gasket 311 is provided to ensure the internal reaction chamber 310 is fully sealed. This unit is disposable or may be stored for archiving once processed. Specimen materials mounted on the inside face of the slide are subjected to reactions within the reaction chamber 310, generally by being contacted with fluid reagents introduced through ports 316a and 316b.

The slide minicassette 302 is configured to removably insert into docking bay 305 of the baseplate module 301, where ports 316a and 316b sealably mate with fluidic channels 306b and 306b. Each fluidic channel is in communication with a bellows pump assembly 322, which includes a diaphragm member and actuation means for drawing fluid from reagent reservoir 307 and into the reaction chamber 310. Generally, bellows pumps 322 and 324 operate in tandem, either by receiving synchronously inverted actuation signals so that one bellows pump is on a downstroke when the other bellows pump is on an upstroke, or the two pumps are operated in alternation. The two pumps may also be operated where one pump is master and the other pump is slave. This configuration is especially useful for elastomeric diaphragms because the slave pump stores stroke energy in the form of stretch of the diaphragm and releases it on the counterstroke. Using these coordinated actuations, which are generally under control of a microprocessor executing a programmable instruction set that is stored in a memory medium in the apparatus or instrument system of which the module is a part, a reciprocating flow regime can be established through the sealed reaction chamber. The chamber typically has a microfluidic "z" dimension wherein diffusional transport is dominant, but the bellows pumps have been shown to be effective in refreshing the boundary layer concentrations above the unstirred layer and thus driving diffusion limited reactions to rapid completion. These systems are also easily automated.

FIG. 25 illustrates a plurality of apparatus modules 300 for use in a carousel or other automated system. Advantageously the modules are mounted in a vertical position to aid in purging bubbles. This demonstrates the suitability for use of the modules in operation of an automated system for processing multiple specimens in parallel.

EXAMPLES

Example 1

Preparation and Assembly of a Microfluidic Assay Device

A microfluidic device for ELISA immunoassay was prepared as follows:
1. Human IgG (0.5 ug in bicarbonate binding buffer pH 9) was deposited onto a plasma-treated test field of a PET sheet. Human IgM was applied as a negative control to a second test field. The proteins were then fixed to the plastic by drying for 5 minutes at 60° C.
2. After fixation, the test fields were blocked for 30 minutes with casein buffer (biotin free) and washed twice with PBST (phosphate buffered saline with 0.1% TWEEN 20).
3. After drying, the treated PET sheets were then assembled between adhesive layers in the microfluidic device of FIG. 3 with integrated pneumatic circuitry for pressurizing the bellows pumps and opening and closing sanitary valves.

Example 2

Performance of an ELISA Immunoassay in a Microfluidic Device

A standard assay for ELISA, useful as a benchmark in method development, involves detection of immobilized human IgG on a solid substrate, followed by blocking and detection of the IgG with biotin-labelled anti-human antibody. The biotin in turn is detected with enzyme-labelled streptavidin.
Procedure:
1. Referring to the microfluidic device prepared as described in Example 1, anti-human IgG biotin (Pierce, 180 uL, 1:10,000 in casein buffer) was added through the sample port, and the device was incubated for 1 min with slow mixing. The test fields were then rinsed with PBST, with slow mixing for 1 min before removing the rinse. A Microflow microfluidics assay instrument (Micronics, Redmond Wash. USA) was used to perform mixing and washing.
2. Detection reagent (Poly SA-HRP) was added with incubation for 1 min with slow mixing. Poly SA-HRP is streptavidin labeled with horseradish peroxidase. The test fields were again washed.
3. TMB (Scytek, TMB High Sensitivity Developing Solution, 180 uL, 1:500 in casein buffer) was added. Following a 2 min incubation to develop color, and a 1 minute wash with PBST, results were scored.
4. A positive reaction was for the IgG test field was indicated by a dark blue precipitate of the diimine.

In this example, TMB (3,3',5,5'-Tetramethylbenzidine) in Citrate/Acetate Buffer was used as the chromogen. Results are shown in the close-up photo insert of FIG. 11. The chamber is described in FIG. 3 and FIG. 9. Note the blue color characteristic of TMB precipitation in the test zone labelled IgG (upper). IgM (lower) was used as a negative control.

Example 3

Assembly of a Microfluidic Device for Immunoassay of Antibodies to Capsular Polysaccharides of *Streptococcus pyogenes*

Assembly of Test Card:
1. Capsular mucosaccharide antigen purified from Group A *Streptococcus pyogenes* is immobilized on a $N_2$ plasma activated polyester sheet by co-polymerization with acrylamide monomer. The sheet is previously masked to define the test field area.
2. The plasma treated test field and surrounding areas are then blocked for 30 minutes with casein buffer and washed twice with PBST (phosphate buffered saline with 0.1% TWEEN 20).
3. After drying, a stack of laminate layers including the antigen-treated polyester sheet are assembled in a microfluidic device generally dimensioned as described in FIG. 9 and assembled with fluidic circuitry per the pattern of FIG. 1.

Example 4

Performance of an Immunodiagnostic Assay in a Microfluidic Device Format

Procedure:
1. Referring to the microfluidic device prepared as described in Example 3, 200 μl of horseradish peroxidase conjugated Group A—*S. pyogenes* anti-capsular antibody in casein buffer is added through the sample port, and the solution is contacted with the test layer with micro-eductive mixing for about 1 min. The test layer is then rinsed 3× with PBST.
2. Develop with 200 μl ABTS and hydrogen peroxide in citrate buffer, pH 3.3. Mix and incubate for 2 minutes followed by a one minute wash with PBST.
3. Positive reactions are indicated by a dark blue precipitate of the diimine which collects on the solid phase affinity capture matrix.

In this example, 2,2'-azino-di-(3-ethylbenzthiazoline sulphonic acid) and 0.03% $H_2O_2$ in 0.1 M citrate buffer pH 4.2 is used as the developing solution. Sensitivity of the assay is improved by use of 0.1% Tween-80 in the rinse (see U.S. Pat. No. 4,810,630) and development solution to retard degradation of the HRP and o-dianisidine to enhance color development.

Example 5

Test Strip for Detection of Antibodies to a Panel of Respiratory Pathogens

Three test areas are negatively masked on a sheet of polystyrene corresponding to a window in a microfluidic device and the plastic is plasma activated. The following antigens, diluted to 2-5 ug/mL, are then immobilized on one each of the test pads:
1. *Streptococcus pneumoniae*, mixed O-serotypes capsular polysaccharide antigens
2. *Streptococcus pyogenes*, Group A capsular antigen
3. Influenza virus, Type A, mixed hemagglutinins H1-H5

The test strip is then blocked and assembled in a sealed microfluidic assay device of FIG. 2. Following preparation of the device, patient serum (1:10 dilution in 180 uL PAABS buffer composed of PBS, 1% BSA, 0.02% sodium azide pH 7.4) is pipetted into the completed microfluidic device through the sample port. The serum is allowed to wet the test pads and the device is incubated 5 min with slow mixing. The test strip is then rinsed 1× with PAABS. A solution of Goat anti-human IgG and Goat anti-human IgM (2:1) at appropriate dilutions in PAABS (200 uL) is added through the sample port and allowed to incubate on the test strip at RT for 20 min. Following incubation, the test strip is rinsed 1× and drained. Detection antibody, a solution of anti-goat IgG conjugated with glucose oxidase, is then applied and incubated at RT for 10 min. Following incubation, the test strip is again rinsed and drained. Development is performed with a solution of nitroblue tetrazolium dye (NBT) in TRIS buffer pH 9.5. A positive serum antibody test is indicated by the development of a blue to purple color on the test strip at the location of one of the antigen pads and is diagnostic of a new or recent infection.

Example 6

Influenza Antigen in a Nasal Lavage

Influenza undergoes a rapid clinical course. Early on, respiratory epithelial lavages contain infectious agent, non-infectious nucleocapsid and envelope debris, and Influenza antigen:IgA complexes. The diagnostic approach taken here involves detection of IgA specific to the Influenza virus. Detection of antibodies is described here.

To prepare horseradish-peroxidase labelled Influenza virus (HPLIV), the method cited by Nielsen is followed [Nielsen, S L et al. 1986. Detection of Immunoglobulin G Antibodies to Cytomegalovirus Antigens by Antibody Capture Enzyme- Linked Immunosorbent Assay. J Clin Microbiol, December 1986, p. 998-1003], but with Influenza virus particles purchased from Fitzgerald Industries (Concord Mass., USA). A microfluidic device is prepared by first immobilizing monoclonal mouse anti-human IgA on the surface of a test strip and blocking with casein-tween blocking solution. The test strip is mounted in a cavity of the device before final assembly. During assembly, the sample reservoir (ie. in a bellows pump chamber) is wetted with 10 ug of HMLIV reagent in 50 uL TBS 1% bovine serum albumin 0.1% Tween 80 (TBSBT) and dried in place under vacuum. Coarsely filtered saline nasal lavage, 2 mL, is buffered with 0.2 mL TRIS to pH 7.4, and the entire volume is transferred to the sample reservoir of the microfluidic device. The material is incubated in place for 2 min to fully dissolve the antigen-conjugate. Sample solution is then passed back and forth across the test field capture site, using the dual bellows system to generate slow reciprocal flow for 2 min. During this process, HRP-labelled virus particles are coated by any IgA antibodies in the sample, and any IgA in the sample is captured by the excess of anti-IgA immobilized on the test strip. After incubation, the device is washed 3× with TBSBT buffer and the rinses drained into the waste reservoir. An adjoining blister pouch (CDRP) fluidly connected to the test chamber contains the color developing reagent. Pressing on a diaphragm overlying the CDRP ruptures the pouch and releases color developing reagent into the test cavity. Development of a blue color precipitate on the test strip is indicative of an immune response, and confirms the presence of immobilized IgA complexes with the HRP-complexed influenza antigen. All mixing and wash steps use eductive mixing.

Example 7

Development of an Agglutination Immunoassay

The microfluidic device used in this assay is that shown in FIG. 7. This card can be used to test two or three reagents against a common liquid bead reagent. As a positive test, anti-human IgG Fc fragment-specific biotin conjugated antibody (Pierce) was dissolved in PBS at a concentration of 24 ug/mL. PBS was used as a negative control. Blue streptavidin-coated beads (Seradyne, 1% solids) suspension was diluted by adding 3 uL of the resuspended beads to 50 uL PBS. The bead solution was placed in a well communicating with each of the test channels. Antibody solution and PBS were placed in test wells at the top of the card. PBS was placed above the left and right channels; antibody solution was placed above the center channel. Using suction pressure generated by a bellows pump, the test solutions and reagent beads were brought into descending serpentine channels in the card and allowed to react as flow continued. There was an immediate strong agglutination reaction in the channel containing streptavidin-coated beads and antibody biotin conjugate. The PBS channel was negative for agglutination. A close up photograph of the results in an assay window is shown in FIG. 12.

Example 8

Agglutination Test for Bladder Tumor Antigen (BTA) in Urine

Clean catch urine is collected for the test at the point of care. Specimens with a specific gravity greater than 1.020 are acceptable for the test. The microfluidics card of FIG. 10 is readily adaptable for the test. Urine is placed in the upper center well. Positive and negative test fluids are place in the side wells. Anti-human BTA IgG conjugated with latex beads is placed in the lower reagent well. The bellows pump is used to initiate flow and mixing of the sample and reagent streams. As each fluid mixes and incubates in the serpentine channels, agglutination of the latex beads observed through the optical window over the center channel indicates a positive immunodiagnosis for the presence of the tumor antigen. The bead reagent fluid is optionally colored to aid the user in following the progress of the assay.

Example 9

Aggutination Test for Enteric Pathogens

Diarrhoeal fluid, 20 mL, which is mostly electrolyte with some mucous, is collected with sterile technique and transferred to a 50 mL polypropylene centrifuge tube. 20 mL of TRIS buffer 0.1M pH 7.0 containing 0.01% thimerosal is added. After light centrifugation in a tabletop centrifuge at 5000 rpm for 10 min to remove grossly visible detritus and mucous strands, the supernatant is decanted into a clean sample container for testing. This solution potentially contains infectious agent and is handled with appropriate precautions. The pretreated sample is analyzed in a diagnostic card of the present invention. Preparation of the card is as follows. Cutouts on thin layers of PET are prepared by laser lithography. Latex beads (Seradyne blue) with antibody to the infectious agents of interest are obtained and resuspended in Citrate 1% BSA 0.1% Triton-X 100 pH 7 lyophilization buffer. The bead suspension is spotted or otherwise applied in the serpentine channels of the card at a concentration sufficient for the assay and is then lyophilized in place. Tests show that this protocol results in a dry bead layer that is readily solubilized by the sample fluid.

In this example, dried beads conjugated with antibody for the following enteric pathogens are used:
1. *Shigella dysenteriae*
2. *Escherichia coli* serotype 0157:H7
3. *Salmonella* sp, polyvalent anti-capsular and flagellar antibody 300 uL of the processed sample is introduced into the sample reservoir of the card. The card is tipped up and tapped to initiate flow, then laid flat or stood on a surface. Fluid exits the sample well through one or more microfluidic channels and makes its way to the larger diameter channels containing the bead lyophilizate. Agglutination in the presence of the appropriate antigen:antibody pairs begins almost immediately as the beads are solubilized in the flow stream. Flow continues through each of the descending serpentine channel to a test field under a window in the card where the results can be read and interpreted. Fluid reaching the waste reservoir is isolated from the user by an elastomeric inner isolation layer, and the reservoir is further isolated with a liquid barrier membrane in the vent as a further safety feature. An absorbent pad in the waste reservoir fills by capillary action, holding the waste. By use of appropriately designed sample ports, and incorporation of a sealed waste receptacle with liquid barrier vent, no potentially biohazardous material is released during the assay. The card is a single-entry closed system and is adapted for applications involving testing for pathogenic microorganisms and parasites. The card is suitable for point-of-care use.

Unless the context requires otherwise, throughout the specification and claims which follow, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

While the above description contains specificities, these specificities should not be construed as limitations on the scope of the invention, but rather as exemplifications of embodiments of the invention. That is to say, the foregoing description of the invention is exemplary for purposes of illustration and explanation. Without departing from the spirit and scope of this invention, one skilled in the art can make various changes and modifications to the invention to adapt it to various usages and conditions without inventive step. As such, these changes and modifications are properly, equitably, and intended to be within the full range of equivalence of the following claims. Thus the scope of the invention should be determined by the appended claims and their legal equivalents, rather than by the examples given.

INCORPORATION BY REFERENCE

All of the U.S. patents, U.S. patent application publications, U.S. patent applications, foreign patents, foreign patent applications and non-patent publications referred to in this specification and related filings are incorporated herein by reference in their entirety.

We claim:

1. An apparatus for sealingly enclosing a first aspect of a substrate member in a reaction chamber, the apparatus comprising:
   a) a baseplate member having a first surface, wherein said first surface comprises a platform medially disposed thereon, said platform having a top surface dimensioned for contactingly receiving the first aspect of the substrate member in juxtaposition with said top surface thereof, and outside edges and outside lateral wall surfaces therearound, wherein said top surface is interrupted by a recess defined by interior walls having a height ranging from 5 to 100 micrometers, a recessed slab connecting the bottom edges of the interior walls, and a boundary ledge connecting the top edges of the interior walls and the outside edges of the platform, said ledge for supporting the first aspect of the substrate member thereon, whereby a reaction chamber with headspace volume is formed between the recessed slab and the first aspect of the substrate member when sealed to said boundary ledge;
   b) a gasket member fitted to the outside edges of said platform, and
   c) a first bellows pump and a second bellows pump located on the first surface, said first bellows pump having a first fluidic connection to said reaction chamber and said second bellows pump having a second fluidic connection to said reaction chamber, at least one of said first and second bellows pumps having one or more fluidic connections to one or more reagent reservoirs or vents disposed outside the reaction chamber, wherein said first fluidic connection and said second fluidic connection pass through the baseplate member.

2. The apparatus of claim 1, wherein said bellows pumps are pneumatically driven and have a positive stroke and a negative suction stroke.

3. The apparatus of claim 1, wherein a reciprocating flow between said first fluidic connection and said second fluidic connection to said reaction chamber is driven by repetitively actuating said first and second bellows pumps by applying a positive pressure pulse to each said bellows pumps in alternation.

4. The apparatus of claim 3, wherein a reciprocating flow between said first fluidic connection and said second fluidic connection to said reaction chamber is driven by actuating said first and second bellows pumps by applying a positive pressure pulse to said first bellows pump and a suction pressure pulse to said second bellows pump, and then reversing the pressure of the pulses applied to each bellows pump.

5. The apparatus of claim 1, wherein said bellows pumps are magnetically driven and have a positive pump stroke and a negative pump stroke, and further wherein a reciprocating flow between said first fluidic connection and said second fluidic connection to said reaction chamber is enabled by inverting the polarity of a first pump stroke of said first bellows pump and a second pump stroke of said second bellows pump in alternation.

6. The apparatus of claim 1, comprising a plurality of pairs of bellows pumps, each bellows pump of said pair having a fluidic connection to said reaction chamber, wherein said pairs are disposed to drive fluid flow across and through said reaction chamber.

7. The apparatus of claim 1, wherein the apparatus comprises an observation window for accessing a viewing area on the substrate member.

8. The apparatus of claim 7, wherein the observation window for accessing a viewing area on the substrate member is formed in said gasket.

9. The apparatus of claim 7, wherein said observation window is proportioned for enabling a bar code label to be applied to the substrate member outside of the viewing area.

10. The apparatus of claim 1, wherein an observation window for accessing a viewing area on the substrate member is formed in said baseplate and extends through said raised platform.

11. The apparatus of claim 1, further comprising a waste outlet in fluid communication with at least one of said bellows pumps.

12. The apparatus of claim 1, wherein the substrate member is a glass slide having a first face on which organic matter is bound.

13. The apparatus of claim 1, wherein the first bellows pump and second bellows pump are disposed proximate to the platform.

14. The apparatus of claim 1, wherein the platform is raised.

15. The apparatus of claim 1, wherein said gasket member is formed of an elastomer, a vinyl rubber, or a silicone.

16. The apparatus of claim 1, wherein said gasket member comprises a stretchable web member for coveringly and sealingly enclosing the substrate member on top of the boundary ledge and a peripheral skirt member for sealingly engaging said outside edges and outside lateral wall surfaces therearound.

17. The apparatus of claim 1, wherein a cutout is formed on a lateral aspect of the gasket member, said cutout for sealedly enclosing the first aspect of the substrate member inside the reaction chamber and a projecting segment of the substrate member outside the reaction chamber.

18. The apparatus of claim 17, wherein said cutout is adapted for receiving a substrate member or glass slide having an electrical junction mounted on the projecting segment of the substrate member or glass slide, said electrical junction connecting to a circuit within said reaction chamber.

\* \* \* \* \*